United States Patent [19]
Baeck et al.

[11] Patent Number: 5,679,630
[45] Date of Patent: Oct. 21, 1997

[54] PROTEASE-CONTAINING CLEANING COMPOSITIONS

[75] Inventors: Andre Baeck, Bonheiden, Belgium; Chanchal Kumar Ghosh, West Chester, Ohio; Thomas Paul Graycar, Pacifica, Calif.; Richard Ray Bott, Burlingame, Calif.; Lori Jean Wilson, Millbrae, Calif.; Philip Frederick Brode, Cincinnati, Ohio; Bobby Lee Barnett, Cincinnati, Ohio; Donn Nelton Rubingh, Cincinnati, Ohio

[73] Assignee: The Procter & Gamble Company, Cincinnati, Ohio

[21] Appl. No.: 322,676

[22] Filed: Oct. 13, 1994

Related U.S. Application Data

[63] Continuation-in-part of Ser. No. 136,797, Oct. 14, 1993, abandoned, and Ser. No. 237,938, May 2, 1994, abandoned.

[51] Int. Cl.$^6$ .................. C11D 7/42; C11D 9/40; C12N 9/54
[52] U.S. Cl. .................. 510/305; 435/221; 510/300
[58] Field of Search .................. 424/94.64, 499; 435/221; 530/350; 252/174.12; 510/305, 306, 320, 321, 392, 530, 226, 235, 300

[56] References Cited

U.S. PATENT DOCUMENTS

| Re. 34,606 | 5/1994 | Estell et al. | 435/222 |
|---|---|---|---|
| 4,634,551 | 1/1987 | Burns et al. | 252/102 |
| 4,686,063 | 8/1987 | Burns et al. | 252/102 |
| 4,760,025 | 7/1988 | Estell et al. | 435/222 |
| 4,914,031 | 4/1990 | Zukowski et al. | 435/222 |
| 4,966,723 | 10/1990 | Hodge et al. | 252/102 |
| 5,069,809 | 12/1991 | Lagenwaard et al. | 252/174.12 |
| 5,118,623 | 6/1992 | Boguslawski et al. | 435/222 |
| 5,155,033 | 10/1992 | Estell et al. | 435/221 |
| 5,182,204 | 1/1993 | Estell et al. | 435/222 |
| 5,185,258 | 2/1993 | Caldwell et al. | 435/220 |
| 5,204,015 | 4/1993 | Caldwell et al. | 252/174.12 |
| 5,324,653 | 6/1994 | van Eekelen et al. | 435/221 |
| 5,336,611 | 8/1994 | van Eekelen et al. | 435/221 |

FOREIGN PATENT DOCUMENTS

| 251446 | 1/1988 | European Pat. Off. | C12N 15/00 |
|---|---|---|---|
| 328229 | 6/1989 | European Pat. Off. | C12N 9/50 |
| 398539 | 11/1990 | European Pat. Off. | C12N 9/54 |
| 405901 | 1/1991 | European Pat. Off. | C11D 3/386 |
| 405902 | 1/1991 | European Pat. Off. | C11D 3/386 |
| 0416967 | 3/1991 | European Pat. Off. | |
| 571 049 | 11/1993 | European Pat. Off. | C12N 15/57 |
| WO88/08028 | 10/1988 | WIPO | C12N 15/00 |
| WO89/04361 | 5/1989 | WIPO | C11D 3/386 |
| WO89/06279 | 7/1989 | WIPO | C12N 9/50 |
| WO89/09819 | 10/1989 | WIPO | C12N 9/54 |
| WO91/00345 | 1/1991 | WIPO | C12N 9/50 |
| WO91/06637 | 5/1991 | WIPO | C12N 9/48 |
| WO92/08778 | 5/1992 | WIPO | C11D 3/386 |
| WO92/11357 | 7/1992 | WIPO | C12N 9/56 |
| WO92/21760 | 12/1992 | WIPO | C12N 15/57 |
| WO94/02618 | 2/1994 | WIPO | C12N 15/57 |
| WO94/10284 | 5/1994 | WIPO | C11D 3/386 |
| WO94/23053 | 10/1994 | WIPO | C12P 9/56 |
| WO95/10615 | 4/1995 | WIPO | C12N 15/57 |

OTHER PUBLICATIONS

Wells et al., "Subtillisin —an enzyme designed to be engineered", TIBS (13), Aug. 1988; pp. 291–297.

Arnold, "Engineering enzymes for non–aqueous solvents", TIBTECH, Sep. 1990 (vol. 8); pp. 244–247.

(List continued on next page.)

*Primary Examiner*—Robert A. Wax
*Assistant Examiner*—Daniel S. Mytelka
*Attorney, Agent, or Firm*—Kim William Zerby; J. J. Yetter; J. C. Rasser

[57] ABSTRACT

The present invention relates to cleaning compositions comprising subtilisin proteases from *Bacillus lentus* having the following alterations: N76D, S103A and V104I, where the numbering is based on the corresponding positions in the subtilisin from *Bacillus amyloliquefaciens*.

7 Claims, 19 Drawing Sheets

OTHER PUBLICATIONS

Wells et al., "Recruitment of substrate–specificity properties from one enzyme into a related one by protein engineering", Proc. Natl. Acad. sci. USA, vol. 84, Aug. 1987; pp. 5167–5171.

Biological Abstracts (9):AB–385 No. 95173, Narhi et al., "Enhanced stability of sutillsin by three point mutations" (Jan. 5, 1991).

Bott, R. et al., "Using Structural Comparison as a Guide in Protein Engineering", Annals of the New York Academy of Sciences, vol. 672, pp. 10–19 (Nov. 30, 1992).

Graycar, Thomas P. et al., "Altering the Proteolytic Activity of Subtillisin through Protein Engineering", Annals of the New York Academy of Sciences, vol. 672, pp. 71–79 (1992).

Siezen, Roland J. et al., "Homology Modelling and Protein Engineering Strategy of Subtilases, the Family of Subtilisin–Like Serine Proteinases", Protein Engineering, vol. 4, No. 7, pp. 719–737 (1991).

Stauffer, C. E. et al., "The Effect on Subtilisin Activity of Oxidizing a Methionine Residue", The Journal of Biological Chemistry, No. 10, vol. 244, pp. 5333–5338 (Oct. 10, 1965).

Pantoliano, Michael W. et al., "Large Increases in General Stability of Subtilins BPN" through Incremental Changes in the Free Energy of Unfolding, Biochemistry 28:7205–7213 (Jun. 21, 1989).

Polgar, Laszlo et al., "Analytical Evidence for the Chemical Transformation of the Essential Serine–221 to Cysteine–221", Biochimica et Biophysica Acta, 667:351–354 (1981).

Svendsen, I.B., "Chemical Modifications of the Subtilisins with Special Reference to the Binding of Large Substrates", Carlsberg Res. Commun., vol. 41, No. 5 pp. 237–291 (1976).

Wells, James A., "Designing Substrate Specificity by Protein Engineering of Electrostatic Interactions", Proc. Natl. Acad. Sci. USA, vol. 84, pp. 1219–1223 (Mar. 1987).

FIG-1B

```
                    -1 ┌→MAT
                       │ 1                                      10
         His Val Ala His Ala Tyr Ala Gln Ser Val Pro Tyr Gly Val Ser Gln Ile Lys Ala Leu His Ser Gln
    399  CAC GTA GCA CAT GCG TAC GCG CAG TCC GTG CCT TAC GGC GTA TCA CAA ATT AAA GCC CTG CAC TCT CAA 20                                     30                                      40
         Gly Tyr Thr Gly Ser Asn Val Lys Val Ala Val Ile Asp Ser Gly Ile Asp Ser Ser His Pro Asn Leu Lys Val
    474  GGC TAC ACT GGA TCA AAT GTT AAA GTA GCG GTT ATC GAT AGC GGT ATC GAT TCT TCT CAT CCT AAT TTA AAG GTA

Pro Asn                            60 Asp
         Ala Gly Gly Ala Ser Met Val Pro Ser Glu Thr Asn Pro Phe Gln Asp Asn Asn Ser His Gly Thr His Val Ala
    549  GCA AGC GGA GCC AGC ATG GTT CCT TCT GAA ACA AAT CCT TTC CAA GAC AAC AAC TCT CAC GGA ACT CAC GTT GCC 70                                      80                              Ser Ala   90
         Gly Thr Val Ala Ala Leu Asn Asn Ser Ile Gly Val Leu Gly Val Ala Pro Ser Ala Ser Leu Tyr Ala Val Lys
    624  GGC ACA GTT GCG GCT CTT AAT AAT TCA ATC GGT GTA TTA GGC GTT GCG CCA AGC GCA TCA CTT TAC GCT GTA AAA

Asp Ala 100                                      110
         Val Leu Gly Ala Asp Gly Ser Gly Gln Tyr Ser Trp Ile Ile Asn Gly Ile Glu Trp Ala Ile Ala Asn Asn Met
    699  GTT CTC GGT GCT GAC GGT TCC GGC CAA TAC AGC TGG ATC ATT AAC GGA ATC GAG TGG GCG ATC GCA AAC AAT ATG 120                                    130                                     140
         Asp Val Ile Asn Met Ser Leu Gly Gly Pro Ser Gly Ser Ala Ala Leu Lys Ala Ala Val Asp Lys Ala Val Ala
    774  GAC GTT ATT AAC ATG AGC CTC GGC GGA CCT TCT GGT TCT GCT GCT TTA AAA GCG GCA GTT GAT AAA GCC GTT GCA

Ser Thr 160
         Ser Gly Val Val Val Ala Ala Ala Gly Asn Glu Gly Thr Ser Gly Ser Ser Ser Thr Val Gly Tyr Pro Gly
    849  TCC GGC GTC GTA GTC GCG GCA GCC GGA AAC GAA GGC ACT TCC GGC AGC AGC TCA ACA GTG GGC TAC CCT GGT
```

```
        170                           180
     Lys Tyr Pro Ser Val Ile Ala Val Gly Ala Val Asp Ser Ser Asn Gln Arp Ala Ser Phe Ser Val Gly Pro
 924 AAA TAC CCT TCT GTC ATT GCA GTA GGC GCT GTT GAC AGC AGC AAC CAA AGA GCA TCT TTC TCA AGC GTA GGA CCT

Glu Leu Asp Val Met Ala Pro Gly Val Ser Ile Gln Ser Thr Leu Pro Gly Asn Lys Tyr Gly Ala Tyr Asn Gly
 999 GAG CTT GAT GTC ATG GCA CCT GGC GTA TCT ATC CAA AGC ACG CTT CCT GGA AAC AAA TAC GGG GCG TAC AAC GGT 220                           230                           240
     Thr Ser Met Ala Ser Pro His Val Ala Gly Aal Ala Ala Leu Ile Leu Ser Lys His Pro Asn Trp Thr Asn Thr
1074 ACG TCA ATG GCA TCT CCG CAC GTT GCC GGA GCG GCT TTG ATT CTT TCT AAG CAC CCG AAC TGG ACA AAC ACT

250 Gln                                                          260
     Gln Val Arp Ser Ser Leu Glu Asn Thr Thr Thr Lys Leu Gly Asp Ser Phe Tyr Tyr Gly Lys Gly Leu Ile Asn
1149 CAA GTC CGC AGC AGT TTA GAA AAC ACC ACT ACA AAA CTT GGT GAT TCT TTG TAC TAT GGA AAA GGG CTG ATC AAC 270     275
     Val Gln Ala Ala Ala Gln DC   TERM
1224 GTA CAA GCG GCA GCT CAG TAA  AACATAAAAAACGGGCCTTGGCCCCGGGTTTTATATTTTCTTCCTCCGATGTTCAATCCGCTCC

1316 ATAATCGACGGATGGCTCCCTCTGAAAATTTAACGAGAAACGGGGTTGACCGGCTCAGTCCCGGTAACGGCCAACTCCTGAAACGTCTCAATCGCCG

1416 CTTCCCGGTTTCCGGTCAGCTCAATGCCATAACGGTCGGCGGCGTTTCCTGATACGGGAGACGGCATTCGTAATCGGATC
```

FIG.-1C

CONSERVED RESIDUES IN SUBTILISINS FROM *BACILLUS AMYLOLIQUEFACIENS*

Comparison of subtilisin sequences from:

B.amyloliquefaciens
B.subtilis
B.licheniformis
B.lentus

```
                10                  20                  30
01  AQSVPYGVSQIKAPALHSQGYTGSNVKVAVIDSGIDSSHP
    AQSVPYGISQIKAPALHSQGYTGSNVKVAVIDSGIDSSHP
    AQTVPYGIPLIKADKVQAQGFKGANVKVAVLDTGIQASHP
    AQSVPWGISRVQAPAAHNRGLTGSGVKVAVLDT*IST*HP 50                  60                  70
41  DLKVAGGASMVPSETNPFQDNNSHGTHVAGTVAALNNSIG
    DLNVRGGASFVPSETNPYQDGSSHGTHVAGTIAALNNSIG
    DLNVVGGASFVAGEAYNTDGNGHGTHVAGTIAALDNTTG
    DLNIRGGASFVPGE*P*STQDGNGHGTHVAGTIAALNNSIG 90                 100                 110
81  VLGVAPSASLYAVKVLGADGSGQYSWIINGIEWAIANNMD
    VLGVSPSASLYAVKVLDSTGSGQYSWIINGIEWAISNNMD
    VVGVAPSVSLYAVKVLNSSGSGSYSGIVSGIEWATTNGMD
    VLGVAPSAELYAVKVLGASGSGSVSSIAQGLEWAGNNGMH 130                 140                 150
121 VINMSLGGPSGSAAALKAAVDKAVASGVVVVAAAGNEGTSG
    VINMSLGGPTGSTALKTVVDKAVSSGIVVAAAAGNEGSSG
    VINMSLGGASGSTAMKQAVDNAYARGVVVVAAAGNSGNSG
    VANLSLGSPSPSATLEQAVNSATSRGVLVVAASGNSGAGS
```

Multiple sequence alignment (residues 161–280, four sequences):

```
     161                       170        180        190        200
Seq1 S  S  T  V  G  Y  P  G  P  K  Y  P  S  V  I  A  V  G  A  V  D  S  S  N  Q  R  A  S  F  S  S  V  G  P  E  L  D  V  M  A
Seq2 S  T  S  V  G  Y  P  A  A  K  Y  P  S  T  I  A  V  G  A  V  D  S  N  S  N  R  A  S  F  S  S  V  G  S  E  L  D  V  M  A
Seq3 S  T  N  -  H  Y  P  A  A  K  Y  P  D  S  V  I  A  V  G  A  V  D  S  N  S  R  R  A  S  F  S  S  V  G  A  E  L  E  V  M  A
Seq4 S  *  *  -  I  G  Y  P  A  R  Y  A  N  A  M  A  V  G  A  T  D  Q  N  N  Q  R  A  S  F  S  Q  Y  G  A  G  L  D  I  V  A 201                      210        220        230        240
Seq1 P  G  V  S  I  Q  S  T  L  P  G  N  K  Y  G  A  Y  N  G  T  S  M  A  S  P  H  V  A  G  A  A  A  A  L  I  L  S  K  H  P  N
Seq2 P  G  V  S  I  Q  S  T  L  P  G  G  T  Y  A  A  Y  N  G  T  S  M  A  T  P  H  V  A  G  A  A  A  A  L  I  L  S  K  H  P  T
Seq3 P  G  A  G  H  V  G  T  T  Y  P  T  N  T  Y  A  L  L  N  G  T  S  M  A  S  P  H  V  A  G  A  A  A  A  L  I  L  K  H  P  N
Seq4 P  G  V  N  V  V  Q  S  Y  P  V  Q  G  S  T  Y  A  S  L  N  G  T  S  M  A  T  P  H  V  A  G  A  A  A  A  L  V  K  Q  N  P  S 241                      250        260        270        280
Seq1 W  T  N  T  Q  V  R  S  S  L  E  N  T  T  T  K  L  G  D  S  F  Y  Y  G  K  G  L  I  N  V  Q  A  A  A  Q
Seq2 T  N  A  Q  Q  R  R  D  L  E  S  S  T  A  T  Y  L  G  N  S  F  Y  Y  G  K  G  L  I  N  V  Q  A  A  A  Q
Seq3 L  S  A  S  Q  V  R  N  R  L  S  S  T  A  T  T  Y  L  G  S  S  F  Y  Y  G  K  G  L  I  N  V  E  A  A  A  Q
Seq4 W  S  N  V  Q  H  I  R  N  H  L  K  N  T  A  T  S  L  G  S  T  N  L  Y  G  S  G  L  V  N  A  E  A  A  T  R
```

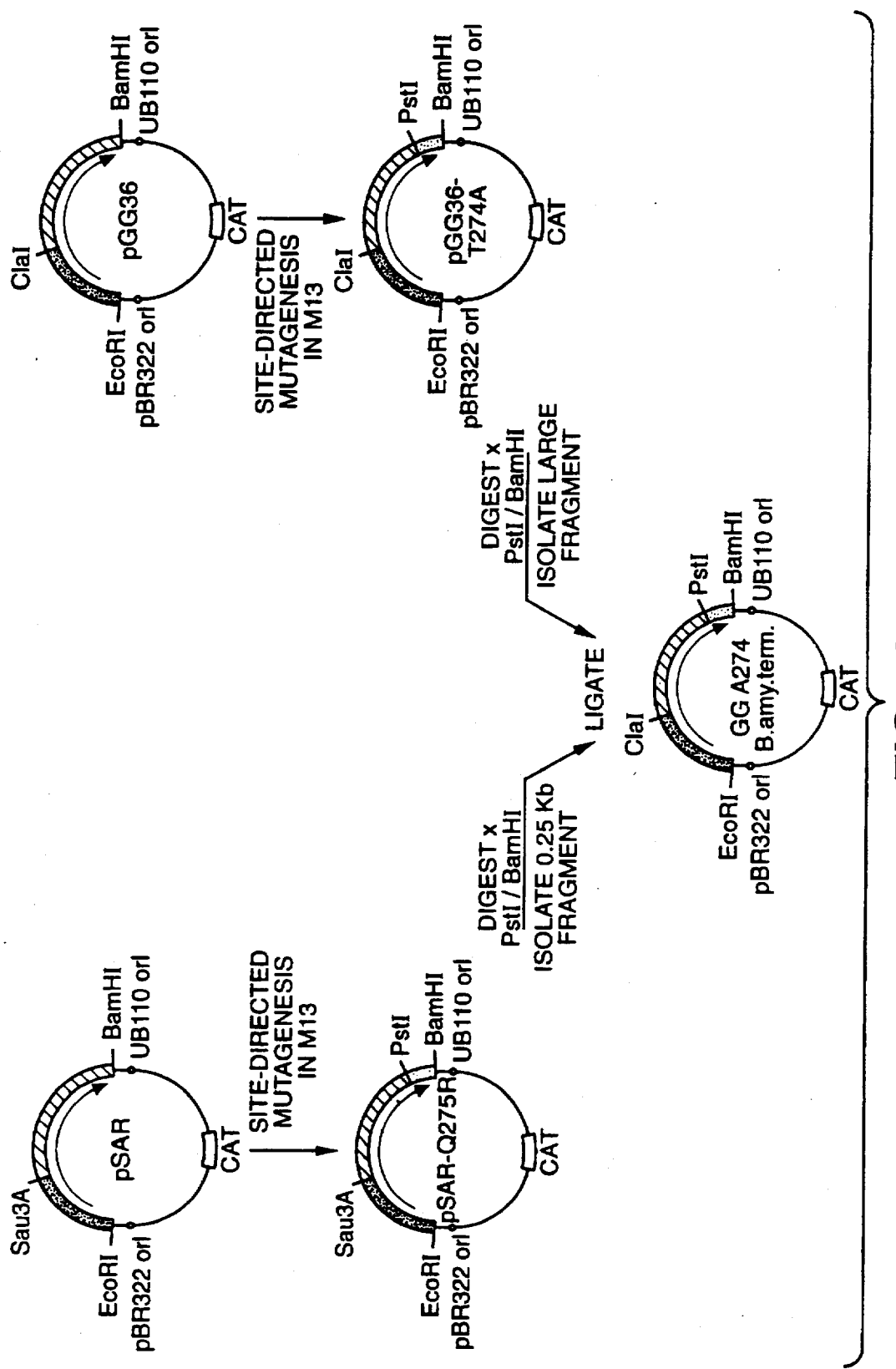
FIG._4

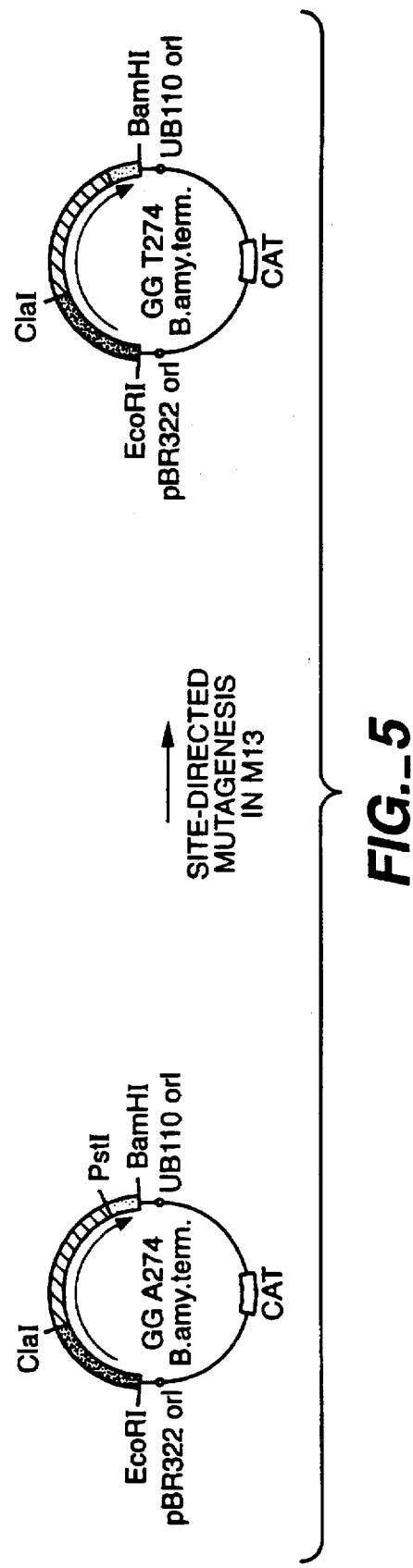
FIG._5

```
         10                         30                        50
ATGAAGAAACCGTTGGGGAAAATTGTCGCAAGCACCGGCACTACTCATTCTGTTGCTTTT
MetLysLysProLeuGlyLysIleValAlaSerThrAlaLeuLeuIleSerValAlaPhe 70                         90                       110
AGTTCATCGATCGCATCGGCTGCTGAAGAAGCAAAAGAAAAAATATTTAATTGGCTTTAAT
SerSerSerIleAlaSerAlaAlaGluGluAlaLysGluLysTyrLeuIleGlyPheAsn 130                        150                       170
GAGCAGGAAGCTGTCAGTGAGTTTGTAGAACAAGTAGAGGCAAATGACGAGGTCGCCATT
GluGlnGluAlaValSerGluPheValGlnValGluAlaAsnAspGluValAlaIle 190                        210                       230
CTCTCTCTGAGGAAGAGGAAGTCGAAATTGAATTGCTTCATGAATTTGAAACGATTCCTGTT
LeuSerLeuArgLysArgLysSerLysLeuAsnCysPheMetAsnLeuLysArgPheLeuVal 250                        270                       290
TTATCCGTTGAGTTAAGCCCAGAAGATGTGGACGCGCTTGAACTCGATCCAGCGATTTCT
LeuSerValGluLeuSerProGluAspValAspAlaLeuGluLeuAspProAlaIleSer 310                        330                       350
TATATTGAAGAGGATGCAGAAGTAACGACAATGGCGCAATCAGTGCCATGGGAATTAGC
TyrIleGluGluAspAlaGluValThrThrMetAlaGlnSerValProTrpGlyIleSer 370                        390                       410
CGTGTGCAAGCCCCAGCTGCCCATAACCGTGGATTGACAGGTTCTGGTGTAAAAGTTGCT
ArgValGlnAlaProAlaAlaHisAsnArgGlyLeuThrGlySerGlyValLysValAla
```

*FIG._6A*

```
                430                          450                           470
GTCCTCGATACAGGTATTTCCACTCATCCAGACTTAAATATTCGTGGTGGCGCTAGCTTT
ValLeuAspThrGlyIleSerThrGlyIleProAspLeuAsnIleArgGlyGlyAlaSerPhe 490                          510                           530
GTACCAGGGGAACCATCCACTCAAGATGGGCATGGCACGCATGGCCGGGACG
ValProGlyGluProSerThrGlnAspGlyAsnGlyHisGlyThrHisValAlaGlyThr 550                          570                           590
ATTGCTGCTTTAAACAATTCGATTGGCGTTCTTGGCGTAGCCCGAGCGCGGAACTATAC
IleAlaAlaLeuAsnAsnSerIleGlyValLeuGlyValAlaAlaProSerAlaGluLeuTyr 610                          630                           650
GCTGTTAAAGTATTAGGGGCCGAGCCGTTCAGGTTCGGTTCAGCTCGATTGCCCAAGGATTG
AlaValLysValLeuGlyAlaSerGlySerValSerSerIleAlaGlnGlyLeu 670                          690                           710
GAATGGGCAGGGAACAATGGCATGCACGTTGCTAATTTGAGTTTAGGAAGCCCTTCGCCA
GluTrpAlaGlyAsnAsnGlyMetHisValAlaAsnLeuSerLeuGlySerProSerPro 730                          750                           770
AGTGCCACACTTGAGCAAGCTGTTAATAGCGCGACTTCTAGAGGCGTTCTTGTTGTAGCG
SerAlaThrLeuGluGlnAlaValAsnSerAlaThrSerArgGlyValLeuValValAla 790                          810                           830
GCATCTGGGAATTCAGGTGCCAGGCTCAATCAGCTATCCGGCCCGTTATGCGAACGCAATG
AlaSerGlyAsnSerGlyAlaGlySerIleSerTyrProAlaArgTyrAlaAsnAlaMet
```

*FIG._6B*

```
850                               870                                890
GCAGTCGGAGCTACTGACCAAAACAACCGGCGCCCAGCTTTTCACAGTATGGCGCAGGG
AlaValGlyAlaThrAspGlnAsnAsnArgAlaSerPheSerGlnTyrGlyAlaGly
        910                             930                              950
CTTGACATTGTCGCACCAGTGTAAACGTGCAGAGCACATACCCAGGTTCAACGTATGCC
LeuAspIleValAlaProGlyValAsnValGlnSerThrTyrProGlySerThrTyrAla
        970                             990                             1010
AGCTTAAACGGTACATCGATGGCTACTCCTCATGTTGCAGGTGCAGCCCTTGTTAAA
SerLeuAsnGlyThrSerMetAlaThrProHisValAlaGlyAlaAlaAlaLeuValLys
       1030                            1050                            1070
CAAAAGAACCCATCTTGGTCCAATGTACAAATCCCAATCATCATCTAAAGAATACGCAACG
GlnLysAsnProSerTrpSerAsnValGlnIleArgAsnHisLeuLysAsnThrAlaThr
       1090                            1110                            1130
AGCTTAGGAAGCACGAACTTGTATGGAAGCGGACTTGTCAATGCAGAAGCGGCAACACGC
SerLeuGlySerThrAsnLeuTyrGlySerGlyLeuValAsnAlaGluAlaAlaThrArg
```

```
                                            10                                    30                                              50
ATGAAGAAACCGTTGGGGAAAATTGTCGCAAGCACCGCCACTACTCATTCTCTGTTGCTTTT
MetLysLysProLeuGlyLysIleValAlaSerThrAlaLeuLeuIleSerValAlaPhe 70                                    90                                             110
AGTTCATCGATCGCATCGGCGCTGCTGAAGAAGCAAAAGAAAAGAAAAATATTTAATTGGCTTTAAT
SerSerSerIleAlaSerAlaAlaGluGluAlaLysGluLysTyrLeuIleGlyPheAsn 130                                   150                                             170
GAGCAGGAAGCTGTCAGTGAGTTTGTAGAACAAGTAGAGGCAAATGACGAGGTCGCCATT
GluGlnGluAlaValSerGluPheValGluGlnValGluAlaAsnAspGluValAlaIle 190                                   210                                             230
CTCTCTGAGGAAGAGGAAGTCGAAATTGCTTCATGAATTTGAAACGATTCCTGTT
LeuSerGluGluGluGluValGluIleGluLeuLeuHisGluPheGluThrIleProVal 250                                   270                                             290
TTATCCGTTGAGTTAAGCCCAGAGATGTGGACGCGCTTGAACTCGATCCAGCGATTCT
LeuSerValGluLeuSerProGluAspValAspAlaLeuGluLeuAspProAlaIleSer 310                                   330                                             350
TATATTGAAGAGGATGCAGAAGTAACGACAATGGCGCAATCAGTGCCATGGGAATTAGC
TyrIleGluGluAspAlaGluValThrThrMetAlaGlnSerValProTrpGlyIleSer 370                                   390                                             410
CGTGTGCAAGCCCCAGCTGCCCATAACCGTGGATTGACAGGTTCTGTGTAAAAGTTGCT
ArgValGlnAlaProAlaAlaHisAsnArgGlyLeuThrGlySerGlyValLysValAla
```

FIG._7A

```
                    430                               450                               470
GTCCTCGATACAGGTATTCCACTCCATCCAGACTTAAATATTCGTGGTGGGCGCTAGCTTT
ValLeuAspThrGlyIleSerThrHisProAspLeuAsnIleArgGlyGlyAlaSerPhe 490                               510                               530
GTACCAGGGGAACCATCCACTCAAGATGGGCATGGCACGCATGGCCGGGACG
ValProGlyGluProSerThrGlnAspGlyHisGlyThrHisValAlaGlyThr 550                               570                               590
ATTGCTGCTTTAGACAACTCGATTGGCGTTCTTGGCGTAGCCGAGCGCGGAACTATAC
IleAlaAlaLeuAspAsnSerIleGlyValLeuGlyValAlaProSerAlaGluLeuTyr 610                               630                               650
GCTGTTAAAGTATTAGGGGCCGAGCGGTTCAGGCGCCATCAGCTCGATTGCCCAAGGATTG
AlaValLysValLeuGlyAlaSerGlyAlaIleSerSerIleAlaGlnGlyLeu 670                               690                               710
GAATGGGCAGGGAACAATGGCATGCAACGTTGCTAATTTGAGTTTAGGAAGCCCTTCGCCA
GluTrpAlaGlyAsnAsnGlyMetHisValAlaAsnLeuSerLeuGlySerProSerPro 730                               750                               770
AGTGCCACACTTGAGCAAGCTGTTAATAGCCGCGACTTCTAGAGGCGTTCTTGTTGTAGCG
SerAlaThrLeuGluGlnAlaValAsnSerAlaThrSerArgGlyValLeuValValAla 790                               810                               830
GCATCTGGGAATTCAGGTGCAGGCTCAATCAGCTATCCGCCCGTTATGCGAACGCAATG
AlaSerGlyAsnSerGlyAlaGlySerIleSerTyrProAlaArgTyrAlaAsnAlaMet
```

*FIG._7B*

```
                                                    850
                          GCAGTCGGAGCTACTGACCAAAACAACAACCGCGCCCAGCTTTTCACAGTATGGGCCAGGG
                          AlaValGlyAlaThrAspGlnAsnAsnArgAlaSerPheSerGlnTyrAlaGly
                                                    910                        890
                          CTTGACATTGTCGCACCAGGTGTAAACGTGCAGAGCACATACCCAGGTTCAACGTATGCC
                          LeuAspIleValAlaProGlyValAsnValGlnSerThrTyrProGlySerThrTyrAla
                                                    970                        950
                          AGCTTAAACGGTACATCGATGGCTACTCCTCATGTTGCAGGTGCAGCCCTTGTTAAA
                          SerLeuAsnGlyThrSerMetAlaThrProHisValAlaGlyAlaAlaLeuValLys
                                                    1030                       1010
                          CAAAGAACCCATCTTGGTCCAATGTACAAATCCGCAATCATCTAAAGAATACGGCAACG
                          GlnLysAsnProSerTrpSerAsnValGlnIleArgAsnHisLeuLysAsnThrAlaThr
                                                    1090                       1070
                          AGCTTAGGAAGCACGAACTTGTATGGAAGCGGACTTGTCAATGCAGAAGCGGCAACACGC
                          SerLeuGlySerThrAsnLeuTyrGlySerGlyLeuValAsnAlaGluAlaAlaThrArg
                                                                               1130
```

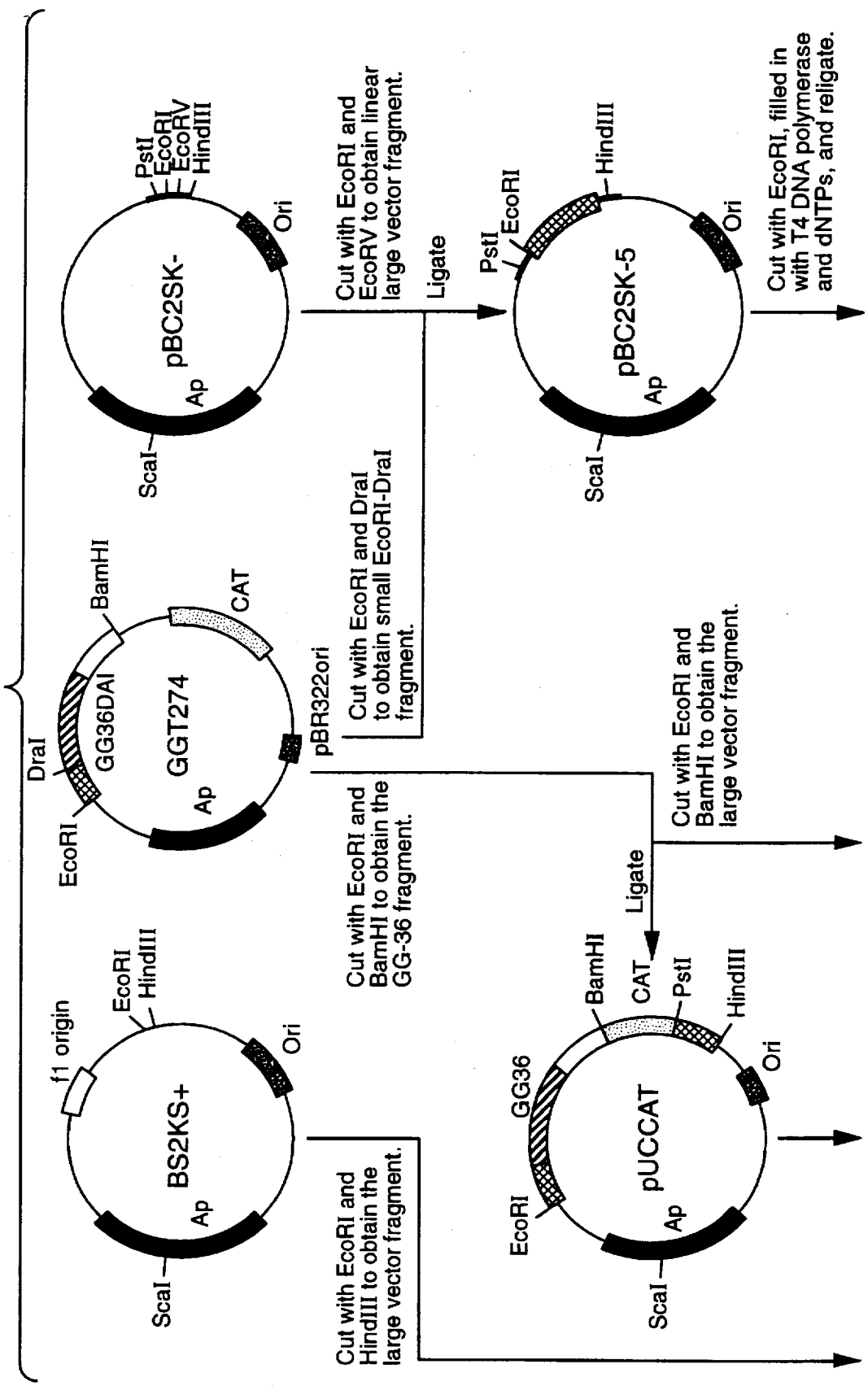
FIG._8A

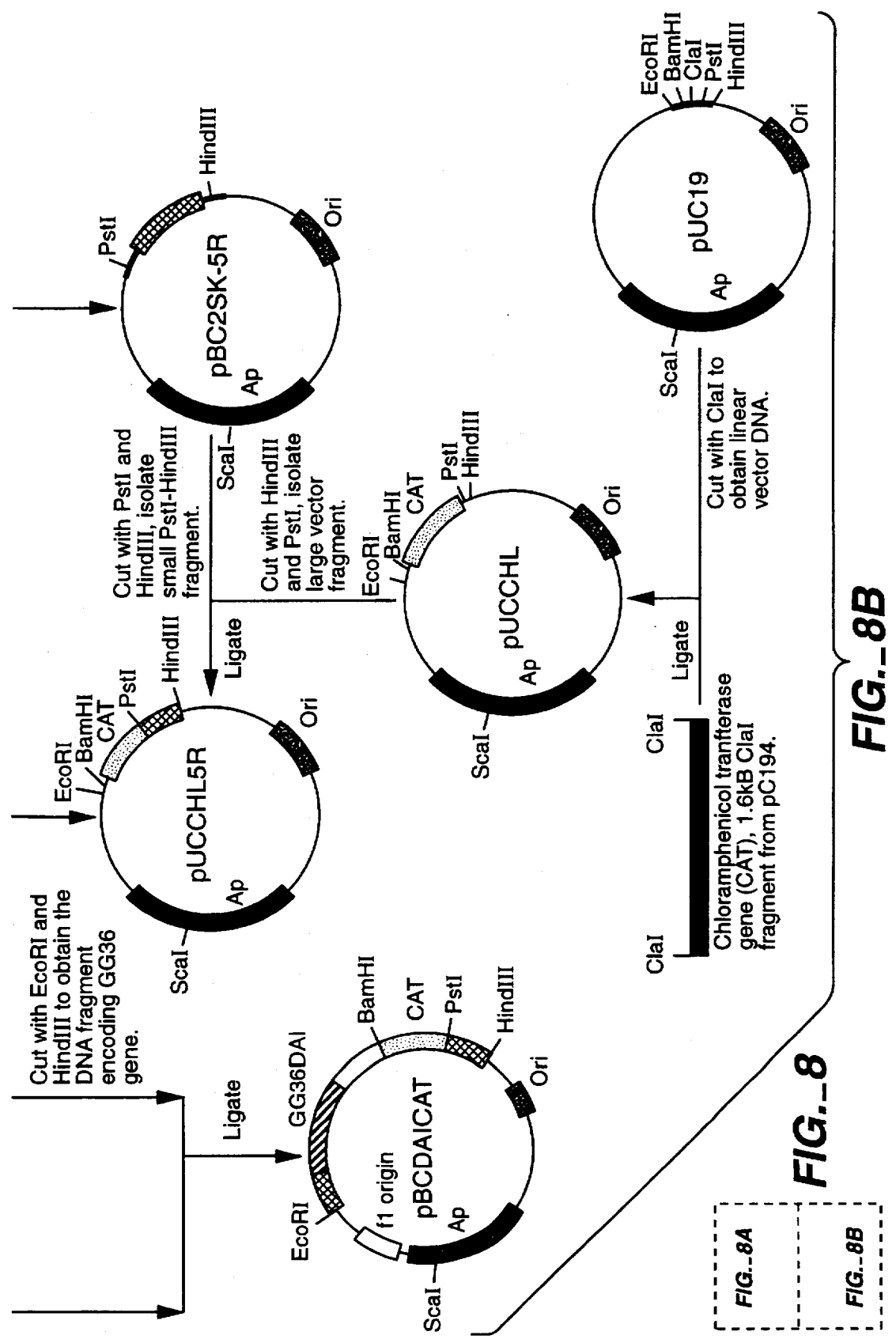
FIG._8B
FIG._8

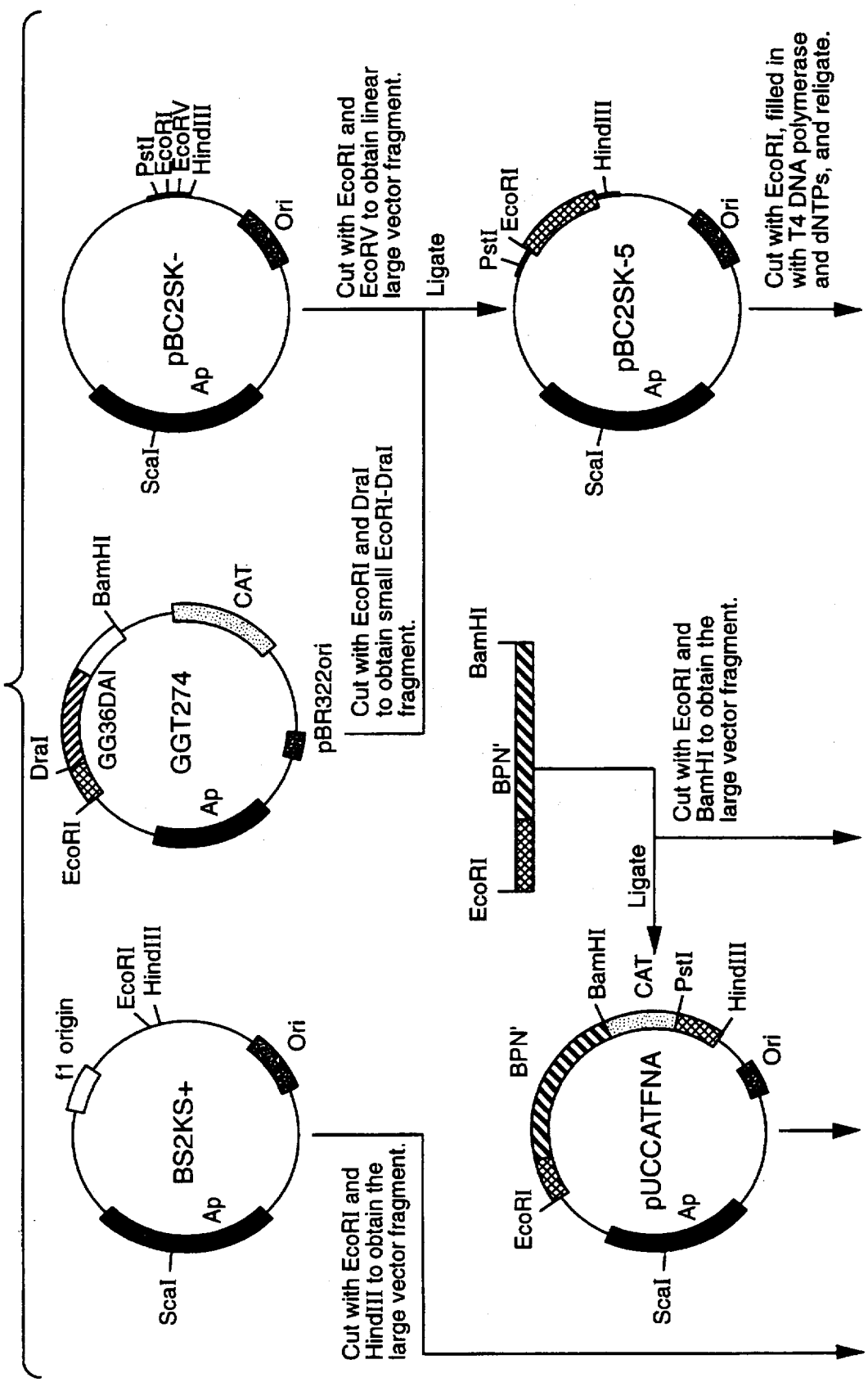
FIG._9A

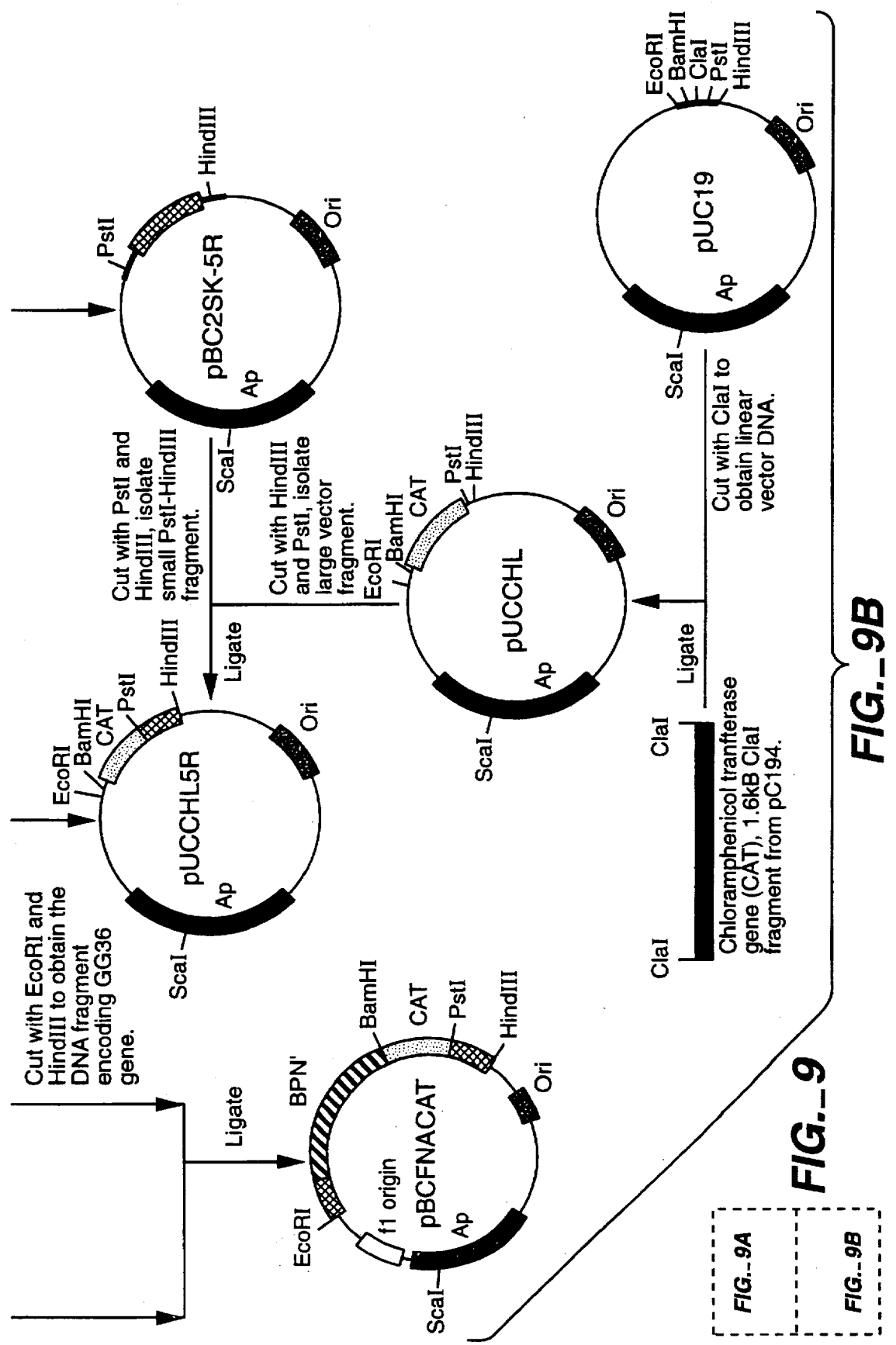
FIG._9B
FIG._9

5,679,630

PROTEASE-CONTAINING CLEANING COMPOSITIONS

This application is a continuation-in-part application of U.S. application Ser. No. 08/136,797, filed Oct. 14, 1993 now abandoned and U.S. application Ser. No. 08/237,938, filed May 2, 1994, now abandoned both incorporated herein by reference in their entirety.

TECHNICAL FIELD

The present invention relates to a variety of cleaning compositions comprising novel protease enzymes which are carbonyl hydrolase variants.

BACKGROUND

Enzymes make up the largest class of naturally occurring proteins. Each class of enzyme generally catalyzes (accelerates a reaction without being consumed) a different kind of chemical reaction. One class of enzymes, known as proteases, are known for their ability to hydrolyze (break down a compound into two or more simpler compounds with the uptake of the H and OH parts of a water molecule on either side of the chemical bond cleaved) other proteins. This ability to hydrolyze proteins has been taken advantage of by incorporating naturally occurring and protein engineered proteases as an additive to laundry detergent preparations. Many stains on clothes are proteinaceous and wide-specificity proteases can substantially improve removal of such stains.

Unfounately, the efficacy level of these proteins in their natural, bacterial environment, frequently does not translate into the relatively unnatural wash environment. Specifically, protease characteristics such as thermal stability, pH stability, oxidative stability and substrate specificity are not necessarily optimized for utilization outside the natural environment of the enzyme.

The amino acid sequence of the protease enzyme determines the characteristics of the protease. A change of the amino acid sequence of the protease may alter the properties of the enzyme to varying degrees, or may even inactivate the enzyme, depending upon the location, nature and/or magnitude of the change in the amino acid sequence. Several approaches have been taken to alter the amino acid sequence of proteases in an attempt to improve their properties, with the goal of increasing the efficacy of the protease for cleaning uses such as in the wash environment. These approaches include altering the amino acid sequence to enhance thermal stability and to improve oxidation stability under quite diverse conditions.

Despite the variety of approaches described in the art, there is a continuing need for new effective variants of proteases useful for cleaning a variety of surfaces. It is therefore an object of the present invention to provide cleaning compositions containing protease enzymes which are carbonyl hydrolase variants having improved proteolytic activity, substrate specificity, stability and/or enhanced performance characteristics. These and other objects will become readily apparent from the detailed description which follows.

SUMMARY OF THE INVENTION

The present invention relates to cleaning compositions comprising:

(a) an effective amount of protease enzyme which is a carbonyl hydrolase variant having an amino acid sequence not found in nature, which is derived by replacement of a plurality of amino acid residues of a precursor carbonyl hydrolase with different amino acids, wherein said plurality of amino acid residues replaced in the precursor enzyme correspond to position +76 in combination with one or more of the following residues: +99, +101, +103, +104, +107, +123, +27, +105, +109, +126, +128, +135, +156, +166, +195, +197, +204, +206, +210, +216, +217, +218, +222, +260, +265, and/or +274, where the numbered positions corresponds to naturally-occurring subtilisin from *Bacillus amyloliquefaciens* or to equivalent amino acid residues in other carbonyl hydrolases or subtilisins (such as *Bacillus lentus* subtilisin); and (b) one or more cleaning composition materials compatable with the protease enzyme.

The present invention also relates to methods for cleaning items in need of cleaning by contacting said item with a protease enzyme which is a carbonyl hydrolase variant as described herein. The invention therefore encompasses a method for cleaning fabrics comprising contacting, preferably with agitation, said fabrics with an aqueous liquor containing said protease enzyme. The method can be carried out at temperatures below about 60° C. but, of course, is quite effective at laundry temperatures up to the boil. The present invention also relates to a method for cleaning dishes by contacting a dish in need of cleaning with a protease enzyme as described herein. The present invention methods also include methods for personal cleansing, said methods comprising contacting the part of the human or lower animal body in need of cleaning with a protease enzyme as described herein.

BRIEF DESCRIPTION OF THE DRAWINGS

FIGS. 1A–C depict the DNA and amino acid sequence for *Bacillus amyloliquefaciens* subtilisin and a partial restriction map of this gene (Seq. ID No.6).

FIG. 2 depicts the conserved amino acid residues among subtilisins from *Bacillus amyloliquefaciens* (BPN)' and *Bacillus lentus* (wild-type).

FIGS. 3A and 3B depict the amino acid sequence of four subtilisins. The top line represents the amino acid sequence of subtilisin from *Bacillus amyloliquefaciens* subtilisin (also sometimes referred to as subtilisin BPN') (Seq. ID No.7). The second line depicts the amino acid sequence of subtilisin from *Bacillus subtills* (Seq. ID No.8). The third line depicts the amino acid sequence of subtilisin from *B. licheniformis* (Seq. ID No.9). The fourth line depicts the amino acid sequence of subtilisin from *Bacillus lentus* (also referred to as subtilisin 309 in PCT WO89/06276) (Seq. ID No. 10). The symbol * denotes the absence of specific amino acid residues as compared to subtilisin BPN'.

FIG. 4 depicts the construction of plasmid GGA274.

FIG. 5 depicts the construction of GGT274 which is an intermediate to certain expression plasmids used in this application.

FIGS. 6A and 6B depict the DNA and amino acid sequence of subtilisin from *Bacillus lentus* (Seq, ID No.11). The mature subtilisin protein is coded by the codons beginning at the codon GCG (334–336) corresponding to Ala.

FIGS. 7A and 7B depict the DNA and amino acid sequence of a preferred embodiment of the invention (N76D/S103AN1041) (Seq. ID No. 12). The DNA in this figure has been modified by the methods described to encode aspartate at position 76, alanine at position 103 and isoleucine at position 104. The mature subtilisin variant protein is coded by the codons beginning at the codon GCG (334-336) corresponding to Ala.

FIG. 8 depicts the construction of vector pBCDAICAT.

FIG. 9 depicts the construction of vector pUCCATFNA.

DETAILED DESCRIPTION OF THE INVENTION

Figure 1A:
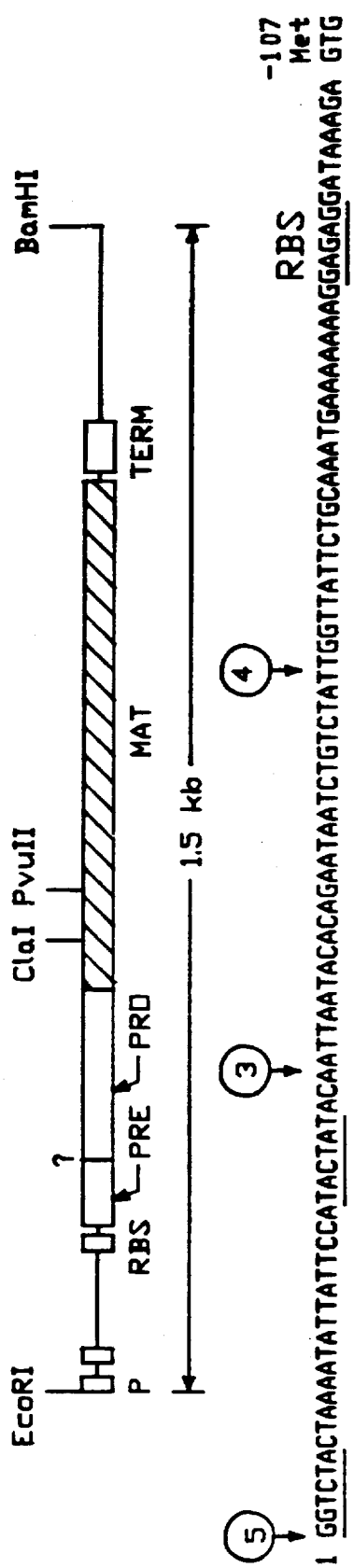

1. Protease Enzymes:

The invention includes protease enzymes which are non-naturally-occurring carbonyl hydrolase variants having a different proteolytic activity, stability, substrate specificity, pH profile and/or performance characteristic as compared to the precursor carbonyl hydrolase from which the amino acid sequence of the variant is derived. The precursor carbonyl hydrolase may be a naturally-occurring carbonyl hydrolase or recombinant hydrolase. Specifically, such carbonyl hydrolase variants have an amino acid sequence not found in nature, which is derived by replacement of a plurality of amino acid residues of a precursor carbonyl hydrolase with different amino acids. The plurality of amino acid residues of the precursor enzyme correspond to position +76 in combination with one or more of the following residues +99, +101, +103, +104, +107, +123, +27, +105, +109, +126, +128, +135, +156, +166, +195, +197, +204, +206, +210, +216, +217, +218, +222, +260, +265, and/or +274, where the numbered position corresponds to naturally-occurring subtilisin from *Bacillus amyloliquefaciens* or to equivalent amino acid residues in other carbonyl hydrolases or subtilisins, such as *Bacillus lentus subtilisin*.

The carbonyl hydrolase variants which are protease enzyme useful in the present invention compositions comprise replacement of amino acid residue +76 in combination with one or more additional modifications. Preferably the variant protease enzymes useful for the present invention comprise the substitution, deletion or insertion of amino acid residues in the following combinations: 76/99; 76/101; 76/103; 76/104; 76/107; 76/123; 76/99/101; 76/99/103; 76/99/104; 76/101/103; 76/101/104; 76/103/104; 76/104/107; 76/104/123; 76/107/123; 76/99/101/103; 76/99/101/104; 76/99/103/104; 76/101/103/104; 76/103/104/123; 76/104/107/123; 76/99/101/103/104; 76/99/103/104/123; 76/99/101/103/104/123; 76/103/104/128; 76/103/104/260; 76/103/104/265; 76/103/104/197; 76/103/104/105; 76/103/104/135; 76/103/104/126; 76/103/104/107; 76/103/104/210; 76/103/104/126/265; and/or 76/103/104/222. Most preferably the variant enzymes useful for the present invention comprise the substitution, deletion or insertion of an amino acid residue in the following combination of residues: 76/99; 76/104; 76/99/104; 76/103/104; 76/104/107; 76/101/103/104; 76/99/101/103/104 and 76/101/104 of *B. amyloliquefaciens* subtilisin.

Variant DNA sequences encoding such carbonyl hydrolase or subtilisin variants are derived from a precursor DNA sequence which encodes a naturally-occurring or recombinant precursor enzyme. The variant DNA sequences are derived by modifying the precursor DNA sequence to encode the substitution of one or more specific amino acid residues encoded by the precursor DNA sequence corresponding to positions 76, 99, 101, 103, 104, 107, 123, 27, 105, 109, 126, 128, 135, 156, 166, 195, 197, 204, 206, 210, 216, 217, 218, 222, 260, 265 and/or 274, in *Bacillus amyloliquefaciens* or any combination thereof. Although the amino acid residues identified for modification herein are identified according to the numbering applicable to *B. amyloliquefaciens* (which has become the conventional method for identifying residue positions in all subtilisins), the preferred precursor DNA sequence useful for the present invention is the DNA sequence of *Bacillus lentus* as shown in FIG. 6 (Seq. ID No. 11).

These variant DNA sequences encode the insertion or substitution of the amino acid residue 76 in combination with one or more additional modification. Preferably the variant DNA sequences encode the substitution or insertion of amino acid residues in the following combinations: 76/99; 76/101; 76/103; 76/104; 76/107; 76/123; 76/99/101; 76/99/103; 76/99/104; 76/101/103; 76/101/104; 76/103/104; 76/104/107; 76/104/123; 76/107/123; 76/99/101/103; 76/99/101/104; 76/99/103/104; 76/101/103/104; 76/103/104/123; 76/104/107/123; 76/99/101/103/104; 76/99/103/104/123; 76/99/101/103/104/123; 76/103/104/128; 76/103/104/260; 76/103/104/265; 76/103/104/197; 76/103/104/105; 76/103/104/135; 76/103/104/126; 76/103/104/107; 76/103/104/210; 76/103/104/126/265; and/or 76/103/1041222. Most preferably the variant DNA sequences encode for the modification of the following combinations of residues: 76/99; 76/104; 76/99/104; 76/103/104; 76/104/107; 76/101/103/104; 76/99/101/103/104 and 76/101/104. These recombinant DNA sequences encode carbonyl hydrolase variants having a novel amino acid sequence and, in general, at least one property which is substantially different from the same property of the enzyme encoded by the precursor carbonyl hydrolase DNA sequence. Such properties include proteolytic activity, substrate specificity, stability, altered pH profile and/or enhanced performance characteristics.

The protease enzymes useful herein encompass the substitution of any of the nineteen naturally occurring L-amino acids at the designated amino acid residue positions. Such substitutions can be made in any precursor subtilisin (procaryotic, eucaryotic, mammalian, etc.). Thoughout this application reference is made to various amino acids by way of common one- and three-letter codes. Such codes are identified in Dale, J. W. (1989), *Molecular Genetics of Bacteria*, John Wiley & Sons, Ltd., Appendix B.

Preferably, the substitution to be made at each of the identified amino acid residue positions include but are not limited to: substitutions at position 76 including D, H, E, G, F, K, P and N; substitutions at position 99 including D, T, N, Q, G and S; substitutions at position 101 including G, D, K, L, A, E, S and R; substitutions at position 103 including Q, T, D, E, Y, K, G, R, S, and A; substitutions at position 104 including all nineteen naturally-occurring amino acids; substitutions at position 107 including V, L, M, Y, G, E, F, T, S, A, N and I; substitutions at position 123 including N, T, I, G, A, C, and S; substitutions at position 27 including K, N, C, V and T; substitutions at position 105 including A, D, G, R and N; substitutions at position 107 including A, L, V, Y, G, F, T, S and A; substitutions at position 109 including S, K, R, A, N and D; substitutions at position 126 including A, F, I, V and G; substitutions at position 128 including G, L and A; substitutions at position 135 including A, F, I, S and V; substitutions at position 156 including D, E, A, G, Q and K; substitutions at position 166 including all nineteen naturally-occurring amino acids; substitutions at position 195 including E; substitutions at position 197 including E; substitutions at position 204 including A, G, C, S and D; substitutions at position 206 including L, Y, N, D and E; substitutions at position 210 including L, I, S, C and F; substitutions at position 216 including V, E, T and K; substitutions at position 217 including all nineteen naturally-occurring amino acids; substitutions at position 218 including S, A, G, T and V; substitutions at position 222 including all nineteen naturally-occurring amino acids; substitutions at position 260 including P, N, G, A, S, C, K and D; substitutions at position 265 including N, G, A, S, C, K, Y and H; and substitutions at position 274 including A and S. The specifically preferred amino acid(s) to be substituted at each such position are designated below in Table I. Although specific amino acids are shown in Table I, it should be understood that any amino acid may be substituted at the identified residues.

TABLE I

| Amino Acid Residue | Preferred Amino Acid to be Substituted/Inserted |
|---|---|
| +76 | D, H |
| +99 | D, T, N, G |
| +101 | R, G, D, K, L, A, E |
| +103 | A, Q, T,D, E, Y, K, G, R |
| +104 | I, Y, S, L, A, T, G, F, M, W, D, V, N |
| +107 | V, L, Y, G, F, T, S, A, N |
| +123 | S, T, I |
| +27 | K |
| +105 | A, D |
| +109 | S, K, R |
| +126 | A, I, V, F |
| +128 | G, L |
| +135 | I, A, S |
| +156 | E, D, Q |
| +166 | D, G, E, K, N, A, F, I, V, L |
| +195 | E |
| +197 | E |
| +204 | A, G, C |
| +206 | L |
| +210 | I, S, C |
| +216 | V |
| +217 | H, I, Y, C, A, G, F, S, N, E, K |
| +218 | S |
| +222 | A, Q, S, C, I, K |
| +260 | P, A, S, N, G |
| +265 | N, A, G, S |
| +274 | A, S |

These protease enzymes containing in vitro mutations in *B. lentus*subtilisin at an amino acid residue equivalent to +76 in *Bacillus amyloliquefaciens* subtilisin produces subtilisin variants exhibiting altered stability (e.g., modified autoproteolytic stability) over precursor subtilisins. (See Tables IV and VI.)

Also, in vitro mutation at residues equivalent to +99, +101, +103, +104, +107, +123, +27, +105, +109, +126, +128, +135, +156, +166, +195, +197, +204, +206, +210, +216, +217, +218, +222, +260, +265, and/or +274 in *Bacillus amyloliquefaciens* subtilisin, alone or in combination with each other and in any combination with +76 mutations, produce subtilisin variants exhibiting altered proteolytic activity, altered thermal stability, altered pH profile, altered substrate specificity and/or altered performance characteristics.

Carbonyl hydrolases are protease enzymes which hydrolyze compounds containing

bonds in which X is oxygen or nitrogen. They include naturally-occurring carbonyl hydrolases and recombinant carbonyl hydrolases. Naturally-occurring carbonyl hydrolases principally include hydrolases, e.g., peptide hydrolases such as subtilisins or metalloproteases. Peptide hydrolases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

"Recombinant carbonyl hydrolase" refers to a carbonyl hydrolase in which the DNA sequence encoding the naturally-occurring carbonyl hydrolase is modified to produce a mutant DNA sequence which encodes the substitution, insertion or deletion of one or more amino acids in the carbonyl hydrolase amino acid sequence. Suitable modification methods are disclosed herein, and in U.S. Pat. No. 4,760,025 (RE 34,606), U.S. Pat. No. 5,204,015 and U.S. Pat. No. 5, 185,258, the disclosure of which are incorporated herein by reference.

Subtilisins are bacterial or fungal carbonyl hydrolases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases the relative order, however, is histidine-aspartate-serine. Thus, subtilisin herein refers to a serine protease having the catalytic triad of subtilisin related proteases. Examples include but are not limited to the subtilisins identified in FIG. 3 herein.

"Recombinant subtilisin" refers to a subtilisin in which the DNA sequence encoding the subtilisin is modified to produce a variant (or mutant) DNA sequence which encodes the substitution, deletion or insertion of one or more amino acids in the naturally-occurring subtilisin amino acid sequence. Suitable methods to produce such modification, and which may be combined with those disclosed herein, include those disclosed in U.S. Pat. No. 4,760,025 (RE 34,606), U.S. Pat. No. 5,204,015 and U.S. Pat. No. 5,185, 258.

"Non-human carbonyl hydrolases" and the DNA encoding them may be obtained from many procaryotic and eucaryotic organisms. Suitable examples of procaryotic organisms include gram negative organisms such as *E. coli* or Pseudomonas and gram positive bacteria such as Micrococcus or Bacillus. Examples of eucaryotic organisms from which carbonyl hydrolase and their genes may be obtained include yeast such as *Saccharomyces cerevisiae*, fungi such as *Aspergillus sp.* and non-human mammalian sources such as, for example, *bovine sp.* from which the gene encoding the carbonyl hydrolase chymosin can be obtained. As with subtilisins, a series of carbonyl hydrolases can be obtained from various related species which have amino acid sequences which are not entirely homologous between the members of that series but which nevertheless exhibit the same or similar type of biological activity. Thus, non-human carbonyl hydrolase as used herein has a functional definition which refers to carbonyl hydrolases which are associated, directly or indirectly, with procaryotic and eucaryotic sources.

A "carbonyl hydrolase variant" has an amino acid sequence which is derived from the amino acid sequence of a "precursor carbonyl hydrolase."The precursor carbonyl hydrolases (such as a subtilisin) include naturally-occurring carbonyl hydrolases (subtilisin) and recombinant carbonyl hydrolases (subtilisin). The amino acid sequence of the carbonyl hydrolase variant is "derived" from the precursor hydrolase amino acid sequence by the substitution, deletion or insertion of one or more amino acids of the precursor amino acid sequence. Such modification is of the "precursor DNA sequence" which encodes the amino acid sequence of the precursor carbonyl hydrolase (subtilisin) rather than manipulation of the precursor carbonyl hydrolase (subtilisin) enzyme per se. Suitable methods for such manipulation of the precursor DNA sequence include methods disclosed herein, as well as methods known to those skilled in the art (see, for example, EP 0 328299, WO89/06279 and the U.S. patents and applications already referenced herein).

Specific residues corresponding to position +76 in combination with one or more of the following positions +99, +101, +103, +104, +107, +123, +27, 105, +109, +126, +128, +135, +156, +166, +195, +197, +204, +206, +210, 216, +217, +218, +222, +260, +265 and/or +274 of *Bacillus amyloliquefaciens* subtilisin are identified herein for mutation. Preferably the modified residues are selected from the following combinations: 76/99; 76/101; 76/103; 76/104; 76/107; 76/123; 76/99/101; 76/99/103; 76/99/104; 76/101/103; 76/101/104; 76/103/104; 76/104/107; 76/104/123; 76/107/123; 76/99/101/103; 76/99/101/104; 76/99/103/104; 76/101/103/104; 76/103/104/123; 76/104/107/123; 76/99/101/103/104; 76/99/103/104/123; 76/99/101/103/104/123; 76/103/104/128; 76/103/104/260; 76/103/104/265; 76/103/104/197; 76/103/104/105; 76/103/104/135; 76/103/104/126; 76/103/104/107; 76/103/104/210; 76/103/104/126/265; and/or 76/103/104/222; and most preferably are 76/99; 76/104; 76/99/104; 76/103/104; 76/104/107; 76/101/103/104; 76/99/101/103/104and 76/101/104. These amino acid position numbers refer to those assigned to the mature *Bacillus amyloliquefaciens* subtilisin sequence presented in FIG. 1. The protease enzymes useful in the present invention, however, are not limited to the mutation of this particular subtilisin but extends to precursor carbonyl hydrolases containing amino acid residues at positions which are "equivalent" to the particular identified residues in *Bacillus amyloliquefaciens* subtilisin Preferably, the precursor subtilisin is *Bacillus lentus* subtilisin and the substitutions, deletions or insertions are made at the equivalent amino acid residue in *B. lentus* corresponding to those listed above.

A residue (amino acid) of a precursor carbonyl hydrolase is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor carbonyl hydrolase is directly compared to the *Bacillus amyloliquefaciens* subtilisin primary sequence and particularly to a set of residues known to be invariant in subtilisins for which sequence is known. FIG. 2 herein shows the conserved residues as between *amyloliquefaciens* subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, in FIG. 3 the amino acid sequence of subtilisin from *Bacillus amyloliquefaciens, Bacillus subtills, Bacillus licheniformis* (carlsbergensis) and *Bacillus lentus* are aligned to provide the maximum amount of homology between amino acid sequences. A comparison of these sequences shows that there are a number of conserved residues contained in each sequence. These conserved residues (as between BPN'and *B. lentus*) are identified in FIG. 2.

These conserved residues, thus, may be used to define the corresponding equivalent amino acid residues of *Bacillus*

*amyloliquefaciens* subtilisin in other carbonyl hydrolases such as subtilisin from *Bacillus lentus* (PCT Publication No. W089/06279 published Jul. 13, 1989), the preferred subtilisin precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Val165 in *Bacillus amyloliquefaciens* subtilisin in the other subtilisins is isoleucine for *B. lentus* and *B. licheniformis.*

Thus, for example, the amino acid at position +76 is asparagine (N) in both *B. amyloliquefaciens* and *B. lentus* subtilisins. In the preferred subtilisin variant useful in the invention, however, the amino acid equivalent to +76 in *Bacillus amyloliquefaciens* subtilisin is substituted with aspartate (D). A comparison of all the amino acid residues identified herein for substitution versus the preferred substitution for each such position is provided in Table II for illustrative purposes.

TABLE II

| | +76 | +99 | +101 | +103 | +104 | +107 | +123 |
|---|---|---|---|---|---|---|---|
| *B. amyloliquefaciens* (wild-type) | N | D | S | Q | Y | I | N |
| *B. lentus* (wild-type) | N | S | S | S | V | I | N |
| Most Preferred Substitution | D | D | R | A | I/Y | V | S |

Equivalent residues may also be defined by determining homology at the level of tertiary structure for a precursor carbonyl hydrolase whose tertiary structure has been determined by x-ray crystallography. Equivalent residues are defined as those for which the atomic coordinates of two or more of the main chain atoms of a particular amino acid residue of the precursor carbonyl hydrolase and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the carbonyl hydrolase in question to the *Bacillus amyloliquefaciens* subtilisin. The best model is the crystallographic model giving the lowest R factor for experimental diffraction data at the highest resolution available.

$$R\ \text{factor} = \frac{\Sigma_h |Fo(h)| - |Fc(h)|}{\Sigma_h |Fo(h)|}$$

Equivalent residues which are functionally analogous to a specific residue of *Bacillus amyloliquefaciens* subtilisin are defined as those amino acids of the precursor carbonyl hydrolases which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor carbonyl hydrolase (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 (equivalent to U.S. patent application Ser. No. 81/212,291, the disclosure of which is incorporated herein by reference) and can be used as outlined above to determine equivalent residues on the level of tertiary structure.

Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. The carbonyl hydrolase variants useful in the present invention include the mature forms of carbonyl hydrolase variants, as well as the pro- and prepro-forms of such hydrolase variants. The prepro-forms are the preferred construction since this facilitates the expression, secretion and maturation of the carbonyl hydrolase variants.

"Prosequence" refers to a sequence of amino acids bound to the N-terminal portion of the mature form of a carbonyl hydrolase which when removed results in the appearance of the "mature" form of the carbonyl hydrolase. Many proteolytic enzymes are found in nature as translational proenzyme products and, in the absence of post-translational processing, are expressed in this fashion. A preferred prosequence for producing carbonyl hydrolase variants, specifically subtilisin variants, is the putative prosequence of *Bacillus amyloliquefaciens* subtilisin, although other subtilisin prosequences may be used. In the Examples, the putative prosequence from the subtilisin from *Bacillus lentus* (ATCC 21536) is used.

A "signal sequence" or "presequence" refers to any sequence of amino acids bound to the N-terminal portion of a carbonyl hydrolase or to the N-terminal portion of a prohydrolase which may participate in the secretion of the mature or pro forms of the hydrolase. This definition of signal sequence is a functional one, meant to include all those amino acid sequences encoded by the N-terminal portion of the subtilisin gene or other secretable carbonyl hydrolases which participate in the effectuation of the secretion of subtilisin or other carbonyl hydrolases under native conditions. The protease enzymes useful for the present invention utilize such sequences to effect the secretion of the carbonyl hydrolase variants as described herein. A preferred signal sequence used in the Examples comprises the first seven amino acid residues of the signal sequence from *Bacillus subtills* subtilisin fused to the remainder of the signal sequence of the subtilisin from *Bacillus lentus* (ATCC 21536).

A "prepro" form of a carbonyl hydrolase variant consists of the mature form of the hydrolase having a prosequence operably linked to the amino terminus of the hydrolase and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, included herein are such other forms of expression vectors which serve equivalent functions and which are, or become, known in the art.

The "host cells" used in the present invention generally are procaryotic or eucaryotic hosts which preferably have been manipulated by the methods disclosed in U.S. Pat. No. 4,760,025 (RE 34,606) to render them incapable of secreting enzymatically active endoprotease. A preferred host cell for expressing subtilisin is the *Bacillus* strain BG2036 which is deficient in enzymatically active neutral protease and alkaline protease (subtilisin). The construction of strain BG2036 is described in detail in U.S. Pat. No. 5,264,366. Other host cells for expressing subtilisin include *Bacillus subtills* I168 (also described in U.S. Pat. No. 4,760,025 (RE 34,606) and U.S. Pat. No. 5,264,366, the disclosure of which are incorporated herein by reference), as well as any suitable Bacillus strain such as *B. licheniformis, B. lentus*, etc.

Host cells are transformed or transfected with vectors constructed using recombinant DNA techniques. Such transformed host cells are capable of either replicating vectors encoding the carbonyl hydrolase variants or expressing the desired carbonyl hydrolase variant. In the case of vectors which encode the pre- or prepro-form of the carbonyl hydrolase variant, such variants, when expressed, are typically secreted from the host cell into the host cell medium.

"Operably linked, " when describing the relationship between two regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor carbonyl hydrolase may be obtained in accord with the general methods known to those skilled in the art. The methods generally comprise synthesizing labeled probes having putative sequences encoding regions of the hydrolase of interest, preparing genomic libraries from organisms expressing the hydrolase, and screening the libraries for the gene of interest by hybridization to the probes. Positively hybridizing clones are then mapped and sequenced. The *B. lentus* gene used in the Examples is cloned as described in Example 1 of U.S. Pat. No. 5,185,258, the disclosure of which is incorporated herein. The BPN' gene used in the Examples is cloned as described in Example 1 in RE 34,606, the disclosure of which is incorporated herein.

The cloned carbonyl hydrolase is then used to transform a host cell in order to express the hydrolase. The hydrolase gene is then ligated into a high copy number plasmid. This plasmid replicates in hosts in the sense that it contains the well-known elements necessary for plasmid replication: a promoter operably linked to the gene in question (which may be supplied as the gene's own homologous promotor if it is recognized, i.e., transcribed, by the host), a transcription termination and polyadenylation region (necessary for stability of the MRNA transcribed by the host from the hydrolase gene in certain eucaryotic host cells) which is exogenous or is supplied by the endogenous terminator region of the hydrolase gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the hydrolase gene into host genome. This is facilitated by procaryotic and eucaryotic organisms which are particularly susceptible to homologous recombination.

The genes used in the present examples are a natural *B. lentus* gene and a natural *B. amyloliquefaciens* gene. Alternatively, a synthetic gene encoding a naturally-occurring or mutant precursor carbonyl hydrolase (subtilisin) may be produced. In such an approach, the DNA and/or amino acid sequence of the precursor hydrolase (subtilisin) is determined. Multiple, overlapping synthetic single-stranded DNA fragments are thereafter synthesized, which upon hybridization and ligation produce a synthetic DNA encoding the precursor hydrolase. An example of synthetic gene construction is set forth in Example 3 of U.S. Pat. No. 5,204,015, the disclosure of which is incorporated herein by reference.

Once the naturally-occurring or synthetic precursor carbonyl hydrolase gene has been cloned, a number of modifications are undertaken to enhance the use of the gene beyond synthesis of the naturally-occurring precursor carbonyl hydrolase. Such modifications include the production of recombinant carbonyl hydrolases as disclosed in U.S. Pat. No. 4,760,025 (RE 34,606) and EPO Publication No. 0 251 446 and the production of carbonyl hydrolase variants described herein.

The following cassette mutagenesis method may be used to facilitate the construction and identification of the carbonyl hydrolase variants useful in the present invention, although other methods including site-directed mutagenesis may be used. First, the naturally-occurring gene encoding the hydrolase is obtained and Sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the hydrolase gene so as to facilitate the replacement of the gene segment. However, any convenient restriction which is not overly redundant in the hydrolase gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, proteolytic activity is defined as the rate of hydrolysis of peptide bonds per milligram of active enzyme. Many well known procedures exist for measuring proteolytic activity (K. M. Kalisz, "Microbial Proteinases," *Advances in Biochemical Engineering/Biotechnology*, A. Fiechter ed., 1988). In addition to or as an alternative to modified proteolytic activity, the variant enzymes of the present invention may have other modified properties such as $K_m$, $K_{cat}$, $K_{cat}/K_m$ ratio and/or modified substrate specificity and/or modified pH activity profile. These enzymes can be tailored for the particular substrate which is anticipated to be present, for example, for hydrolytic processes such as laundry uses.

One objective can be to secure a variant carbonyl hydrolase having altered proteolytic activity as compared to the precursor carbonyl hydrolase, since increasing such activity (numerically larger) enables the use of the enzyme to more efficiently act on a target substrate. Also of interest are variant enzymes having altered thermal stability and/or altered substrate specificity as compared to the precursor. Preferably the carbonyl hydrolase to be mutated is a subtilisin. Specific amino acids useful to obtain such results in subtilisin-type carbonyl hydrolases at residues equivalent to +76, +99, +101, +103, +104, +107, +123, +27, +105, +109, +126, +128, +135, +156, +166, +195, +197, +204, +206, +210, +216, +217, +218, +222, +260, +265 and/or +274 or any combination thereof in *Bacillus amyloliquefaciens* subtilisin are presented in the Examples. In some instances, lower proteolytic activity may be desirable. Conversely, in some instances it may be desirable to increase the proteolytic activity of the variant enzyme versus its precursor. Additionally, increases or decreases (alteration) of the stability of the variant, whether alkaline or thermal stability, may be desirable. Increases or decreases in $K_{cat}$, $K_m$ or $K_{cat}/K_m$ are specific to the substrate used to determine these kinetic parameters.

Also, it has been determined that residues equivalent to +76 in combination with a number of other modifications in subtilisin are important in modulating overall stability and/or proteolytic activity of the enzyme. Thus, as set forth in the Examples, the Asparagine (N) in *Bacillus lentus* subtilisin at equivalent position +76 can be substituted with Aspartate (D) in the preferred protease enzymes in combination with modification of one or more of the following amino acid residues +99, +101, +103, +104, +107, +123, +27, +105, +109, +126, +128, +135, +156, +166, +195, +197, +204, +206, +210, +216, +217, +218, +222, +260, +265and/or +274to produce enhanced stability and/or enhanced activity of the resulting mutant enzyme.

The most preferred protease enzymes useful in this invention are set forth in the Examples. These include the following specific combinations of substituted residues: N76D/ S99D; N76D/V104I; N76D/S99D/V104I; N76D/S103A/ V104I; N76D/V104I/I107V; N76D/V104Y/I107V and N76D/S101R/S103AN104I. These substitutions are preferably made in *Bacillus lentus* (recombinant or native-type) subtilisin, although the substitutions may be made in any *Bacillus* subtilisin.

Based on the results obtained with this and other variant subtilisins, it is apparent that residues in carbonyl hydrolases (preferably subtilisin) equivalent to positions +76, +99, +101, +103, +104, +107, +123, +27, +105, +109, +126, 128, +135, +156, +166, +195, +197, +204, +206, +210, +216, +217, +218, 222, +260, +265 and/or +274 in *Bacillus amyloliquefaciens* are important to the proteolytic activity, performance and/or stability of these enzymes and the cleaning or wash performance of such variant enzymes.

The following is presented by way of example for manufacturing protease enzymes useful in the present invention compositions.

Protease Manufacture Example

Construction for the Expression of GG36 Gene in *B. subtilis*

The cloning and the construction for expression of the subtilisin gene from *B. lentus* is performed essentially the same as that described in U.S. Pat. No. 5,185,258. The plasmid GGA274 (described in FIG. 4 herein) is further modified in the following manner, as shown in FIG. 5. The PstI site that is introduced during the construction of the GGA274 plasmid is removed by the oligonucleotide directed mutagenesis described below, with an oligonucleotide having the following sequence: 5' GAAGCTGCA ACTCGTTAAATAAA 3' (Seq. ID No.1). The underlined "A" residue eliminates the recognition sequence of restriction enzyme PstI and changes the corresponding amino acid residue from alanine to threonine at position 274. Threonine at position 274 is the wild-type residue originally found in the cloned B. lentus subtilisin gene sequences. The DNA segment encoding subtilisin is excised from the plasmid GGA274 or its derivatives (GGT274 shown in FIG. 5) by EcoRI and BamHI digest. The DNA fragment is subcloned back into Bacteriophage M13-based vectors, such as MP19, for mutagenesis. After mutagenesis, the EcoRI and HindIII digest, followed by cloning, are performed to move the mutated subtilisin gene back into an expression plasmid like GGA274 for the expression and the recovery of mutated subtilisin proteins.

Oligonucleotide-Directed Mutagenesis

Oligonucleotide-directed mutagenesis is performed as described in Zoller, M. et al. (1983), Methods Enzymol., 100:468–500. As an example, a synthetic oligonucleotide of the sequence 5'GCTGCTCTAGACAATTCG 3' (Seq. ID No.2) is used to change the amino acid residue at position 76 from asparagine (N) to aspartic acid (D), or N76D. The underlined "G" and "C" residues denote changes from the wild-type gene sequence. The CA keeps the leucine at position +75 and changes the amino acid sequence to introduce an XbaI recognition site of the XbaI restriction enzyme (TCTAGA), while the change at GAC changes asparagine at +76 to aspartate.

For mutagenesis at positions 99, 101, 103 and 104, different oligonucleotides can be used depending on the combination of mutations desired. For example, an oligonucleotide of the sequence 5' GTATTAGGGGCGGACG-GTCGAGGCGCCATCAGCTCGATT 3' (Seq. ID No.3) is used to simultaneously make the following changes: S99D; S101R; S103A and V104I in a single subtilisin molecule. Similarly, oligonucleotides of the sequence 5' TCAGGT-TCGGTCTCGAGCGTTGCCCAAGGATTG 3' (Seq. ID No.4) and 5' CACGTTGCTAGCTTGAGTTTAG 3' (Seq. ID No.5) are utilized to generate I107V and N123S, respectively. Again, the underlined residues denote changes from wild-type sequences which produce desired changes either in amino acid sequences or restriction enzyme recognition sequences.

Proteolytic Activity of Subtilisin Variants

Following the methods of Oligonucleotide-Directed Mutagenesis hereinbefore, the variants listed in Table III are made. Proteolytic activity of each of these subtilisin variants is shown in Table III. The kinetic parameters $K_{cat}$, $K_M$, and $K_{cat}/K_M$ are measured for hydrolysis of the synthetic peptide substrate succinyl-L-Ala-L-Ala-L-Pro-L-Phe-p-nitroanilide using the method described in P. Bonneau et al. (1991) J. Am. Chem. Soc., Vol. 113, No. 3, p. 1030. Briefly, a small aliquot of subtilisin variant stock solution is added to a 1 cm cuvette containing substrate dissolved in 0.1M Tris-HCL buffer pH 8.6 and thermostated at 25° C. The reaction progress is followed spectrophotometrically by monitoring the absorbance of the reaction product p-nitroaniline at 410 nm. Kinetic parameters are obtained by using a non-linear regression algorithm to fit the reaction velocity and product concentration for each reaction to the Michaelis-Menten equation.

TABLE III

Kinetic Parameters $k_{cat}$, $K_M$ and $k_{cat}/K_M$
Measured for Bacillus lentus Subtilisin and Variants

| Protease # | Enzyme Variants | $k_{cat}$ $(s^{-1})$ | $K_M$ (M) | $k_{cat}/K_M$ $(s^{-1}M^{-1})$ |
|---|---|---|---|---|
| — | B. lentus Subtilisin | 170 | 0.0078 | $2.18 \times 10^5$ |
| — | N76D | 219 | 0.008 | $2.74 \times 10^5$ |
| 1 | N76D/S99D | 88 | 0.00061 | $1.44 \times 10^5$ |
| 2 | N76D/S101R | 371 | 0.0013 | $2.85 \times 10^5$ |
| 3 | N76D/S103A | 400 | 0.0014 | $2.86 \times 10^5$ |
| 4 | N76D/V104I | 459 | 0.0011 | $4.17 \times 10^5$ |
| 5 | N76D/I107V | 219 | 0.0011 | $1.99 \times 10^5$ |
| 6 | N76D/N123S | 115 | 0.0018 | $6.40 \times 10^5$ |
| 7 | N76D/S99D/S101R | 146 | 0.00038 | $3.84 \times 10^5$ |
| 8 | N76D/S99D/S103A | 157 | 0.0012 | $1.31 \times 10^5$ |
| 9 | N76D/S99D/V104I | 247 | 0.00097 | $2.55 \times 10^5$ |
| 10 | N76D/S101R/S103A | 405 | 0.00069 | $5.90 \times 10^5$ |
| 11 | N76D/S101R/V104I | 540 | 0.00049 | $1.10 \times 10^5$ |
| 12 | N76D/S103A/V104I | 832 | 0.0016 | $5.20 \times 10^5$ |
| 13 | N76D/V104I/I107V | 497 | 0.00045 | $1.10 \times 10^6$ |
| 14 | N76D/V104Y/I107V | 330 | 0.00017 | $1.90 \times 10^6$ |
| 15 | N76D/V104I/N123S | 251 | 0.0026 | $9.65 \times 10^4$ |
| 16 | N76D/I107V/N123S | 147 | 0.0035 | $4.20 \times 10^4$ |
| 17 | N76D/S99D/S101R/S103A | 242 | 0.00074 | $3.27 \times 10^5$ |
| 18 | N76D/S99D/S101R/V104I | 403 | 0.00072 | $5.60 \times 10^5$ |
| 19 | N76D/S99D/S103A/V104I | 420 | 0.0016 | $2.62 \times 10^5$ |
| 20 | N76D/S101R/S103A/V104I | 731 | 0.00065 | $1.12 \times 10^6$ |
| 21 | N76D/S103A/V104I/N123S | 321 | 0.0026 | $1.23 \times 10^5$ |
| 22 | N76D/V104I/I107V/N123S | 231 | 0.003 | $7.70 \times 10^4$ |
| 23 | N76D/S99D/S101R/S103A/V104I | 624 | 0.00098 | $6.37 \times 10^5$ |
| 24 | N76D/S99D/S103A/V104I/N123S | 194 | 0.0043 | $4.51 \times 10^4$ |
| 25 | N76D/S99D/S101R/S103A/V104I/N123S | 311 | 0.0023 | $1.35 \times 10^5$ |

The results listed in Table III indicate that all of the subtilisin variants tested retain proteolytic activity. Further, detailed analysis of the data reveal that proteolytic activity is significantly altered for Bacillus lentus subtilisin by the various combinations of substitutions at amino acid residues equivalent to positions 76, 99, 101, 103, 104, 107 and 123 in Bacillus amyloliquefaciens.

Thermal Stability of Subtilisin Variants

A comparison of thermal stability observed for Bacillus lentus subtilisin and the variants of the present invention made by the process of Oligonucleotide-Directed Mutagenesis hereinbefore is shown in Table IV. Purified enzyme, 15 ug/ml in 0.1M glycine 0.01% Tween-80 pH 10.0, with or without 50 mM $CaCl_2$, is aliquotted into small tubes and incubated at 10° C. for 5minutes, 10° C. to 60° C. over 1 minute, and 60° C. for 20 minutes. Tubes are then placed on ice for 10 minutes. Aliquots from the tubes are assayed for enzyme activity by addition to 1 cm cuvettes containing 1.2 mM of the synthetic peptide substrate succinyl-L-ala-L-Ala-L-Pro-L-Phe-p-nitroanilide dissolved in 0.1M tris-HCL buffer, pH 8.6, thermostatted at 25° C. The initial linear reaction velocity is followed spectrophotometrically by monitoring the absorbance of the reaction product p-nitroaniline at 410 nm as a function of time. Data are presented as percent activity prior to heating. The results listed in Table IV indicate that a vast majority of variants exhibit thermal stability comparable to Bacillus lentus subtilisin (24 out of 26) in the test condition with 50 mM $CaCl_2$ added. In the test condition without 50 mM $CaCl_2$ added, a vast majority of variants (19 out of 26) are significantly more stable than Bacillus lentus subtilisin. Further, the variants N76D/S99D, N76D/V104I, N76D/S99D/V104I, N76D/ S103A/V104I, N76D/V104I/I107V, N76D/V104Y/I107V and N76D/S101R/S103A/V104I are significantly more stable than the single substitution variant N76D in the test condition without 50 mM CaCl₂ added.

TABLE IV

Thermal Stability Measured for *Bacillus lentus* Subtilisin and Variants at pH 10, 60° C., +/−50 mM CaCl₂ Added

| Enzyme | % Initial Activity Remaining | |
|---|---|---|
|  | −CaCl₂ | +CaCl₂ |
| *B. lentus* Subtilisin | 2 | 96 |
| N76D | 34 | 97 |
| N76D/S99D | 49 | 98 |
| N76D/S101R | 0 | 82 |
| N76D/S103A | 26 | 92 |
| N76D/V104I | 58 | 98 |
| N76D/I107V | 32 | 96 |
| N76D/N123S | 0 | 97 |
| N76D/S99D/S101R | 30 | 100 |
| N76D/S99D/S103A | 36 | 100 |
| N76D/S99D/V104I | 48 | 97 |
| N76D/S101R/S103A | 26 | 100 |
| N76D/S101R/V104I | 38 | 100 |
| N76D/S103A/V104I | 58 | 100 |
| N76D/V104I/I107V | 60 | 97 |
| N76D/V104Y/I107V | 48 | 74 |
| N76D/V104I/N123S | 0 | 98 |
| N76D/I107V/N123S | 16 | 100 |
| N76D/S99D/S101R/S103A | 38 | 100 |
| N76D/S99D/S101R/V104I | 33 | 100 |
| N76D/S99D/S103A/V104I | 38 | 98 |
| N76D/S101R/S103A/V104I | 40 | 99 |
| N76D/S103A/V104I/N123S | 1 | 98 |
| N76D/V104I/I107V/N123S | 3 | 99 |
| N76D/S99D/S101R/S103A/V104I | 36 | 99 |
| N76D/S99D/S103A/V104I/N123S | 2 | 95 |
| N76D/S99D/S101R/S103A/V104I/N123S | 0 | 100 | pUCCHL5R to make pUCCAT. The large EcoRI-HindIII fragment of pUCCAT is then cloned into the EcoRI and HindIII sites of BS2KS+ to generate the plasmid pBCDA-ICAT.

To generate single-stranded DNA, *E. coli*-containing pBCDAICAT are infected with phage R408 (obtained from Stratagene, San Diego, Calif.) following the protocol described in Russel, M., Kidd, S. and Kelley, M. R., GENE 45:333–338 1986. Once the single-stranded DNA template is available, standard mutagenesis methods as described above in Oligonucleotide-Directed Mutogenesis are carried out. The construction of certain mutants is detailed below for illustrative purposes.

For the construction of *B. lentus* (GG36) N76D/S103A/V104I/L217H, an EcoRI-BamHI DNA fragment encoding GG36N76D/S103A/V104I is used in the construction of pUCCAT (see FIG. 8) to generate the plasmid pBCDAICAT. After the single-stranded DNA template is made following the protocol described above, a mutagenesis primer with the following sequence

```
                     * **** ** xClaI
5' TAT GCC AGC CAC AAC GGT ACT TCG ATG GCT 3' (Seq. ID No. 13)
```

Oligonucleotide-Directed Mutagenesis with Single-Stranded DNA Template Generated from Phagemid A. Construction of *B. lentus* Variants The mutagenesis protocol is essentially the same as described above in Oligonucleotide-Directed Mutagenesis. The single-stranded DNA template is generated by phagemid method. To construct the phagemid vector for generating the single-stranded DNA template we first construct the vector pBCDAICAT. The flow chart of vector construction is outlined in FIG. 8. First, the ClaI to ClaI fragment encoding the CAT gene from pC194 plasmid (Horinouchi, S. and Weisblum, B., *J. Bacteriol.*, 150:8–15, 1982) is cloned into the AccI site of polylinker region of pUC19 (New England BioLabs, Beverly, Mass.) to make plasmid pUCCHL and the EcoRI-DraI 0.6 KB fragment from the 5' end of the GG36DAI encoding DNA is cloned into the EcoRI and EcoRV sites of pBSKS plasmid (Stratagene, Inc., San Diego, Calif.) to make pBC2SK5. The single EcoRI site of the plasmid pBC2SK5 is eliminated by EcoRI digestion, followed by filling in catalyzed-by-T4 DNA polymerase, and religation to generate the plasmid pBC2SK-5R which does not have the EcoRI site. The EcoRI-DraI fragment which is cloned into pBCSK-5R is isolated as a PstI-HindIII fragment and cloned into the PstI-HindIII site of the pUCCHL (part of the polylinker of pUC19) to generate plasmid pUCCHL5R. The encoding sequence of GG36DAI gene is excised as an EcoRI-BamHI fragment and cloned into the EcoRI-BamHI sites of is used to make the L217H. As before, the underlined residues denote the nucleotide changes that are made and the × ClaI indicates that the existing ClaI site is eliminated after the mutagenesis. The mutagenesis protocol is as described in Oligonucleotide-Directed Mutagenesis hereinbefore. After the mutagenesis, plasmid DNA is first screened for the elimination of the ClaI site and those clones missing the ClaI site are subjected to DNA sequence analysis to verify the DNA sequence which made the L to H change at the 217th amino acid residue.

B. Construction of BPN' Variants and their Expression in *B. subtilis*

The construction of *B. amyloliquefaciens* (BPN') N76D/Q103A/Y104I/Y217L is done in a similar fashion except in two consecutive steps. N76D is first introduced into BPN' Y217L to make BPN' N76D/Y217L and a second mutagenesis is done to convert BPN' N76D/Y217L to BPN' N76D/Q103A/Y104I/Y217L. To generate the single-stranded DNA template for the first mutagenesis, an EcoRI-BamHI fragment encoding BPN' Y217L subtilisin (derived from the Y217L plasmid described in Wells, J., et al., PNAS, 84, 5167, 1087) is used to construct a plasmid pUCCATFNA (see FIG. 9). The pUCCATFNA plasmid containing BPN' Y217L is used to construct the pBCFNACAT plasmid (FIG. 9). Single-stranded DNA is generated as described above. To generate BPN' N76D/Y217L, an oligonucleotide primer with the sequence

```
* *** ** XbaI
     5' C ACA GTT GCG GCT CTA GAT AAC TCA ATC GGT G 3'(Seq. ID No.14)
``` is used to generate the change N76D. Single-stranded DNA is then prepared from the pBCFNACAT plasmid containing the BPN' N76D/Y217L (the pBCFNACAT plasmid after N76D mutagenesis) and mutagenized with another oligonucleotide with the sequence

```
* *** ** x PvuII
     5' GCT GAC GGT TCC GGC GCT ATT AGT TGG ATC ATT 3' (Seq. ID No. 15)
``` to obtain BPN' N76D/Q103A/Y104I/Y217L. All steps involved in the cloning, the single-stranded DNA preparation, the mutagenesis, and the screening for mutants are carried out as described above. Expression of the BPN' gene and its variants are achieved by integrating plasmid DNA (pBCFNACAT containing the different variants' BPN' gene) directly into a protease-deficient strain of *Bacillus subtilis* as described in RE 34,606.

Numerous variants are made as per the teachings of these Protease Manufacture Examples. Kinetics data and stability data are generated for such variants. The kinetics data are generated using the methods described hereinbefore and are provided in Table V. The stability data are generated as detailed herein. Results are shown in Table VI.

Thermal Stability Assay Procedure

Purified enzyme is buffer-exchanged into 0.1M glycine pH 10.0, 0.01% Tween-80 by applying the enzyme to a column consisting of Sephadex G-25 equilibrated with this buffer and eluting the enzyme from the column using the same buffer.

To a tube containing 0.1M glycine, 0.01% Tween-80 pH 10.0 thermostatted at 60° C., the buffer-exchanged enzyme is added to give a final enzyme concentration of 15 ug/ml.

Aliquots are removed from the 60° C. incubation at various times and immediately assayed for enzyme activity by addition to a 1 cm cuvette containing 1.2 mM of the synthetic peptide substrate succinyl-L-Ala-L-Ala-L-Pro-L-Phe-p-nitroanilide dissolved in 0.1M tris-HCL buffer, pH 8.6, thermostatted at 25° C. The initial linear reaction velocity is followed spectrophotometrically by monitoring the absorbance of the reaction product p-nitroaniline at 410 nm as a function of time.

Half-life, which is the length of time required for 50% enzyme inactivation, is determined from the first-order plot of reaction velocity as a function of the time of incubation at 60° C.

The data are presented in Table VI as percent of the half-life determined for *Bacillus lentus* subtilisin (GG36) under identical conditions,

TABLE V

| Enzyme | kcat (s$^{-1}$) | KM (mM) | kcat/KM (s$^{-1}$M$^{-1}$) |
| --- | --- | --- | --- |
| B. lentus subtilisin | 170 | 0.78 | 2.20E + 05 |
| N76D/S103G/V104I* | 380 | 1.4 | 2.70E + 05 |
| N76D/S103A/V104F | 730 | 0.33 | 2.20E + 06 |
| N76D/S103A/V104N | 790 | 2.8 | 2.80E + 05 |
| N76D/S103A/V104S | 170 | 0.83 | 2.00E + 05 |
| N76D/S103A/V104T | 370 | 1.9 | 2.00E + 05 |
| N76D/S103A/V104W | 880 | 0.31 | 2.80E + 06 |
| N76D/S103A/V104Y | 690 | 0.5 | 1.40E + 06 |
| K27R/N76D/V104Y/N123S | 500 | 1.2 | 4.20E + 05 |
| N76D/S101G/S103A/V104I* | 620 | 1.3 | 4.80E + 05 |

TABLE V-continued

| Enzyme | kcat (s$^{-1}$) | KM (mM) | kcat/KM (s$^{-1}$M$^{-1}$) |
| --- | --- | --- | --- |
| N76D/S103A/V104I/S105A* | 550 | 1.3 | 4.20E + 05 |
| N76D/S103A/V104I/S105D* | 440 | 1.7 | 2.60E + 05 |
| N76D/S103A/V104T/I107A* | 120 | 5.7 | 2.10E + 04 |
| N76D/S103A/V104T/I107L* | 310 | 3.2 | 9.70E + 04 |
| N76D/S103A/V104I/L126A | 90 | 2.2 | 4.10E + 04 |
| N76D/S103A/V104I/L126F | 180 | 1.9 | 9.50E + 04 |
| N76D/S103A/V104I/L126I | 100 | 2.4 | 4.20E + 04 |
| N76D/S103A/V104I/L126V | 64 | 3.2 | 2.00E + 04 |
| N76D/S103A/V104I/S128G* | 560 | 1.7 | 3.30E + 05 |
| N76D/S103A/V104I/S128L* | 430 | 3.8 | 1.10E + 05 |
| N76D/S103A/V104I/L135A | 140 | 0.76 | 1.80E + 05 |
| N76D/S103A/V104I/L135F | 390 | 0.69 | 5.70E + 05 |
| N76D/S103A/V104I/L135I | 110 | 0.73 | 1.50E + 05 |
| N76D/S103A/V104I/L135V | 140 | 0.86 | 1.60E + 05 |
| N76D/S103A/V104I/S156E* | 170 | 2.6 | 6.50E + 04 |
| N76D/S103A/V104I/S166D* | 160 | 3.5 | 4.60E + 04 |
| N76D/S103A/V104I/D197E | 510 | 1.4 | 3.60E + 05 |
| N76D/S103A/V104I/N204A* | 530 | 1.1 | 4.80E + 05 |
| N76D/S103A/V104I/N204G* | 580 | 1.4 | 4.10E + 05 |
| N76D/S103A/V104I/N204C* | 370 | 1.3 | 2.90E + 05 |
| N76D/S103A/V104I/P210I* | 500 | 1.2 | 4.20E + 05 |
| N76D/S103A/V104I/L217H* | 80 | 0.63 | 1.30E + 05 |
| N76D/S103A/V104I/M222A | 70 | 3.1 | 2.30E + 04 |
| N76D/S103A/V104I/M222S | 80 | 3.1 | 2.60E + 04 |
| N76D/S103A/V104I/T260P | 660 | 1.5 | 4.40E + 05 |
| N76D/S103A/V104I/S265N | 590 | 1.3 | 4.50E + 05 |
| K27R/N76D/V104Y/I107V/N123S | 220 | 1.4 | 1.60E + 05 |
| K27R/N76D/V104Y/N123S/D197E | 430 | 1.1 | 3.90E + 05 |
| K27R/N76D/V104Y/N123S/N204C | 400 | 1.1 | 3.60E + 05 |
| K27R/N76D/V104Y/N123S/Q206L | 440 | 1.2 | 3.70E + 05 |
| K27R/N76D/V104Y/N123S/S216V | 440 | 1.2 | 3.70E + 05 |
| K27R/N76D/V104Y/N123S/N218S | 760 | 0.98 | 7.80E + 05 |
| K27R/N76D/V104Y/N123S/T260P | 410 | 1.2 | 3.40E + 05 |
| K27R/N76D/V104Y/N123S/T274A | 390 | 1 | 3.90E + 05 |
| N76D/S103A/V104I/L126F/S265N | 170 | 2.1 | 8.10E + 04 |
| N76D/S103A/V104I/S156E/S166D* | 40 | 6.3 | 6.40E + 03 |
| K27R/N76D/V104Y/N123S/G195E/G197E | 410 | 0.98 | 4.20E + 05 |
| K27R/N76D/V104Y/N123S/G195E/N218S | 540 | 0.66 | 8.20E + 05 |
| K27R/N76D/V104Y/N123S/D197E/N218S | 770 | 0.79 | 9.80E + 05 |
| K27R/N76D/V104Y/N123S/N204C/N218S | 610 | 0.99 | 6.20E + 05 |
| K27R/N76D/V104Y/N123S/Q206L/N218S | 580 | 0.78 | 7.40E + 05 |
| K27R/N76D/V104Y/N123S/N218S/T260P | 660 | 1 | 6.60E + 05 |
| K27R/N76D/V104Y/N123S/N218S/T274A | 590 | 0.89 | 6.60E + 05 |
| K27R/N76D/V104Y/Q109S/N123S/N218S/T274A | 520 | 1 | 5.20E + 05 |
| K27R/N76D/V104Y/N123S/G195E/D197E/N218S | 460 | 0.65 | 7.10E + 05 |
| B. amyloliquefaciens subtilisin (BPN') | 50 | 0.14 | 3.60E + 05 |
| BPN'-N76D/Y217L* | 380 | 0.46 | 8.30E + 05 |

*These mutants are made as per Oligonucleotide-Directed Mutagenesis with Single-Stranded DNA Template Generated from Phagemid, all others made as per Oligonucleotide-Directed Mutagenesis, hereinbefore.

TABLE VI

| Enzyme | Thermal Stability (% half-life of native enzyme) |
|---|---|
| B. lentus subtilisin | 100 |
| N76D | 590 |
| N76D/S99D | 840 |
| N76D/S103A | 390 |
| N76D/V104I | 660 |
| N76D/I107V | 710 |
| N76D/N123S | 70 |
| N76D/S99D/S101R | 610 |
| N76D/S99D/S103A | 590 |
| N76D/S99D/V104I | 910 |
| N76D/S101R/S103A | 930 |
| N76D/S101R/V104I | 500 |
| N76D/S103A/V104I | 460 |
| N76D/S103G/V104I* | 370 |
| N76D/S103A/V104F | 480 |
| N76D/S103A/V104N | 230 |
| N76D/S103A/V104S | 230 |
| N76D/S103A/V104T | 370 |
| N76D/S103A/V104W | 280 |
| N76D/SI03A/V104Y | 400 |
| N76D/V104I/I107V | 940 |
| N76D/V104Y/I107V | 820 |
| N76D/V104I/N123S | 80 |
| N76D/I107V/N123S | 150 |
| K27R/N76D/V104Y/N123S | 100 |
| N76D/S99D/S101R/S103A | 570 |
| N76D/S99D/S101R/V104I | 1000 |
| N76D/S99D/S103A/V104I | 680 |
| N76D/S101G/S103A/V104I* | 390 |
| N76D/S101R/S103A/V104I | 470 |
| N76D/S103A/V104I/S105A* | 360 |
| N76D/S103A/V104I/S105D* | 370 |
| N76D/S103A/V104T/I107A* | 270 |
| N76D/S103A/V104T/I107L* | 230 |
| N76D/S103A/V104I/N123S | 110 |
| N76D/V104I/I107V/N123S | 220 |
| N76D/S103A/V104I/L126A | 270 |
| N76D/S103A/V104I/L126F | 950 |
| N76D/S103A/V104I/L126I | 410 |
| N76D/S103A/V104I/L126V | 320 |
| N76D/S103A/V104I/S128G* | 640 |
| N76D/S103A/V104I/S128L* | 760 |
| N76D/S103A/V104I/L135A | 230 |
| N76D/S103A/V104I/L135F | 200 |
| N76D/S103A/V104I/L135I | 510 |
| N76D/S103A/V104I/L135V | 500 |
| N76D/S103A/V104I/S156E* | 120 |
| N76D/S103A/V104I/S166D* | 590 |
| N76D/S103A/V104I/D197E | 460 |
| N76D/S103A/V104I/N204A* | 230 |
| N76D/S103A/V104I/N204G* | 240 |
| N76D/S103A/V104I/N204C* | 500 |
| N76D/S103A/V104I/P210I* | 1370 |
| N76D/S103A/V104I/L217H* | 60 |
| N76D/S103A/V104I/M222A | 520 |
| N76D/S103A/V104I/M222S | 490 |
| N76D/S103A/V104I/T260P | 490 |
| N76D/S103A/V104I/S265N | 360 |
| K27R/N76D/V104Y/I107V/N123S | 210 |
| K27R/N76D/V104Y/N123S/D197E | 120 |
| K27R/N76D/V104Y/N123S/N204C | 110 |
| K27R/N76D/V104Y/N123S/Q206L | 380 |
| K27R/N76D/V104Y/N123S/S216V | 140 |
| K27R/N76D/V104Y/N123S/N218S | 270 |
| K27R/N76D/V104Y/N123S/T260P | 40 |
| K27R/N76D/V104Y/N123S/T274A | 60 |
| N76D/S99D/S101R/S103A/V104I | 590 |
| N76D/S99D/S103A/V104I/N123S | 110 |
| N76D/S103A/V104I/L126F/S265N | 810 |
| N76D/S103A/V104I/S156E/S166D* | 220 |
| K27R/N76D/V104Y/N123S/G195E/G197E | 90 |
| K27R/N76D/V104Y/N123S/G195E/N218S | 250 |
| K27R/N76D/V104Y/N123S/D197E/N218S | 270 |
| K27R/N76D/V104Y/N123S/N204C/N218S | 460 |
| K27R/N76D/V104Y/N123S/Q206L/N218S | 1400 |
| K27R/N76D/V104Y/N123S/N218S/T260P | 310 |
| K27R/N76D/V104Y/N123S/N218S/T274A | 180 |
| N76D/S99D/S101R/S103A/V104I/N123S | 90 |
| K27R/N76D/V104Y/Q109S/N123S/N218S/T274 | 230 |
| K27R/N76D/V104Y/N123S/G195E/D197E/N21 | 240 |
| B. amyloliquefaciens subtilisin (BPN') | 100 |
| BPN'-N76D/Y217L* | 420 |

*These mutants are made as per Oligonucleotide-Directed Mutagenesis with Single-Stranded DNA Template Generated from Phagemid, all others made as per Oligonucleotide-Directed Mutagenesis, hereinbefore.

2. Cleaning Composition Materials:

The cleaning compositions of the present invention also comprise, in addition to the protease enzyme described hereinbefore, one or more cleaning composition materials compatible with the protease enzyme. The term "cleaning composition materials", as used herein, means any liquid, solid or gaseous material selected for the particular type of cleaning composition desired and the form of the product (e.g., liquid; granule; spray composition), which materials are also compatible with the protease enzyme used in the composition. The specific selection of cleaning composition materials are readily made by considering the surface, item or fabric to be cleaned, and the desired form of the composition for the cleaning conditions during use (e.g., through the wash detergent use). The term "compatible", as used herein, means the cleaning composition materials do not reduce the proteolytic activity of the protease enzyme to such an extent that the protease is not effective as desired during normal use situations. Specific cleaning composition materials are exemplified in detail hereinafter.

An effective amount of one or more protease enzymes described above are included in compositions useful for cleaning a variety of surfaces in need of proteinaceous stain removal. Such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form); oral cleaning compositions, unlimited in form (e.g., dentifrice, toothpaste and mouthwash formulations); and denture cleaning compositions, unlimited in form (e.g., liquid, tablet). As used herein, "effective amount of protease enzyme" refers to the quantity of protease enzyme described hereinbefore necessary to achieve the enzymatic activity necessary in the specific cleaning composition. Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like.

Preferably the cleaning compositions of the present invention comprise from about 0.0001% to about 10% of one or more protease enzymes, more preferably from about 0.001% to about 1%, more preferably still from about 0.001% to about 0.1%. Several examples of various cleaning compositions wherein the protease enzymes may be employed are discussed in further detail below. All parts, percentages and ratios used herein are by weight unless otherwise specified.

As used herein, "non-fabric cleaning compositions" include hard surface cleaning compositions, dishwashing compositions, oral cleaning compositions, denture cleaning compositions and personal cleansing compositions.

A. Cleaning Compositions for Hard Surfaces Dishes and Fabrics

The protease enzymes can be used in any detergent composition where high sudsing and/or good insoluble substrate removal are desired. Thus the protease enzymes can be used with various conventional ingredients to provide fully-formulated hard-surface cleaners, dishwashing compositions, fabric laundering compositions and the like. Such compositions can be in the form of liquids, granules, bars and the like. Such compositions can be formulated as modern "concentrated" detergents which contain as much as 30%–60% by weight of surfactants.

The cleaning compositions herein can optionally, and preferably, contain various anionic, nonionic, zwitterionic, etc., surfactants. Such surfactants are typically present at levels of from about 0.1% to about 60%, preferably from about 1% to about 35%, of the compositions.

Nonlimiting examples of surfactants useful herein include the conventional $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)x(CHOSO_3)^- M^+)CH_3$ and $CH_3(CH_2)y(CHOSO_3^-M^+) CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1-7 ethoxy sulfates), $C_{10}$–$C_{18}$ alkyl alkoxy carboxylates (especially the EO 1-7 ethoxycarboxylates), the $C_{10}$–$C_{18}$ alkyl polyglycosides, and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, $C_8$–$C_{24}$ sarcosinates (especially oleoyl sarcosinate), and the like. The alkyl alkoxy sulfates (AES) and alkyl alkoxy carboxylates (AEC) are preferred herein. (Use of such surfactants in combination with the aforesaid amine oxide and/or betaine or sultaine surfactants is also preferred, depending on the desires of the formulator.) Other conventional useful surfactants are listed in standard texts. Particularly useful surfactants include the $C_{10}$–$C_{18}$N-methyl glucamides disclosed in U.S. Pat. No. 5, 194,639, Connor et al., issued Mar. 16, 1993, incorporated herein by reference.

Particularly useful is the class of nonionic surfactants which are condensates of ethylene oxide with a hydrophobic moiety to provide a surfactant having an average hydrophilic-lipophilic balance (HLB) in the range from 5 to 17, preferably from 6 to 14, more preferably from 7 to 12. The hydrophobic (lipophilic) moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements. Especially preferred are the $C_9$–$C_{15}$ primary alcohol ethoxylates (or mixed ethoxy/propoxy) containing 3–8 moles of ethylene oxide per mole of alcohol, particularly the $C_{14}$–$C_{15}$ primary alcohols containing 6–8 moles of ethylene oxide per mole of alcohol, the $C_{12}$–$C_{15}$ primary alcohols containing 3-5 moles of ethylene oxide per mole of alcohol, and mixtures thereof A wide variety of other ingredients useful in detergent cleaning compositions can be included in the compositions herein, including other active ingredients, carriers, hydrotropes, processing aids, dyes or pigments, solvents for liquid formulations, etc. If an additional increment of sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additional sudsing.

The liquid detergent compositions herein can contain water and other solvents as carriers. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about to about 90%, typically from about 10% to about 50% of such carriers.

The detergent compositions herein will preferably be formulated such that during use in aqueous cleaning operations, the wash water will have a pH between about 6.8 and about 11.0. Finished products thus are typically formulated at this range. Techniques for controlling pH at recommended usage levels include the use of buffers, alkalis, acids, etc., and are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases, peroxidases, and proteases in such compositions, typically at levels of from about 0.001% to about 1% by weight. Various detersive and fabric care enzymes are well-known in the laundry detergent art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various dye transfer inhibiting agents, such as polyvinyl pyrrolidone, various suds suppressors, especially silicones and secondary alcohols, various fabric softeners, especially smectite clays and clay floculating polymers (e.g., poly(oxy ethylene)), and the like can all be used in such compositions at levels ranging from about 1% to about 35% by weight. Standard formularies and published patents contain multiple, detailed descriptions of such conventional materials.

Enzyme stabilizers may also be used in the cleaning compositions of the present invention. Such enzyme stabilizers include propylene glycol (preferably from about 1% to about 10%), sodium formate (preferably from about 0.1% to about 1%) and calcium formate (preferably from about 0.1% to about 1%).

1. Hard surface cleaning compositions

As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more protease enzymes, preferably from about 0.0001% to about 10%, more preferably from about 0.001% to about 5%, more preferably still from about 0.001% to about 1% by weight of active protease enzyme of the composition. In addition to comprising one or more protease enzymes, such hard surface cleaning compositions typically comprise a surfactant and a water-soluble sequestering builder. In certain specialized products such as spray window cleaners, however, the surfactants are sometimes not used since they may produce a filmy/streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%. Preferably the pH should be in the range of about 8 to 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3pentanediol and 2-ethyl-1,3-hexanediol. When used, such solvents are typically present at levels of from about 0.5% to about 15%, preferably from about 3% to about 11%.

Additionally, highly volatile solvents such as isopropanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

The hard surface cleaning composition embodiment of the present invention is illustrated by the following nonlimiting examples. (In the following examples, reference to "Protease #" in the examples is to the variant useful in the present invention compositions having the given number in Table III hereinbefore.)

EXAMPLES 1–6

| | Liquid Hard Surface Cleaning Compositions | | | | | |
|---|---|---|---|---|---|---|
| | Example No. | | | | | |
| Component | 1 | 2 | 3 | 4 | 5 | 6 |
| Protease #12 | 0.05 | 0.20 | 0.02 | 0.03 | 0.10 | 0.03 |
| Protease #4 | — | — | — | — | 0.20 | 0.02 |
| EDTA** | — | — | 2.90 | 2.90 | — | — |
| Na Citrate | — | — | — | — | 2.90 | 2.90 |
| NaC$_{12}$ Alkyl-benzene sulfonate | 1.95 | — | 1.95 | — | 1.95 | — |
| NaC$_{12}$ Alkylsulfate | — | 2.20 | — | 2.20 | — | 2.20 |
| NaC$_{12}$ (ethoxy)*** sulfate | — | 2.20 | — | 2.20 | — | 2.20 |
| C$_{12}$ Dimethylamine | — | 0.50 | — | 0.50 | — | 0.50 |

-continued

| | Liquid Hard Surface Cleaning Compositions | | | | | |
|---|---|---|---|---|---|---|
| | Example No. | | | | | |
| Component | 1 | 2 | 3 | 4 | 5 | 6 |
| oxide | | | | | | |
| Na Cumene sulfonate | 1.30 | — | 1.30 | — | 1.30 | — |
| Hexyl Carbitol*** | 6.30 | 6.30 | 6.30 | 6.30 | 6.30 | 6.30 |
| Water**** | | | balance to 100% | | | |

**Na$_4$ ethylenediamine diacetic acid
***Diethyleneglycol monohexyl ether
****All formulas adjusted to pH 7

In Examples 1–4 the Proteases #'s 1–11 and 13–25 recited in Table III, among others including the additional proteases useful in the present invention described in Tables V and VI, are substituted for Protease #12, with substantially similar results.

In Examples 5 and 6, any combination of the protease enzymes useful in the present invention recited in Tables III, V and VI, among others, are substituted for Protease #12 and Protease #4, with substantially similar results.

EXAMPLES 7–12

| | Spray Compositions for Cleaning Hard Surfaces and Removing Household Mildew | | | | | |
|---|---|---|---|---|---|---|
| | Example No. | | | | | |
| Component | 7 | 8 | 9 | 10 | 11 | 12 |
| Protease #12 | 0.20 | 0.05 | 0.10 | 0.30 | 0.20 | 0.30 |
| Protease #4 | — | — | — | — | 0.30 | 0.10 |
| Sodium octyl sulfate | 2.00 | 2.00 | 2.00 | 2.00 | 2.00 | 2.00 |
| Sodium dodecyl sulfate | 4.00 | 4.00 | 4.00 | 4.00 | 4.00 | 4.00 |
| Sodium hydroxide | 0.80 | 0.80 | 0.80 | 0.80 | 0.80 | 0.80 |
| Silicate (Na) | 0.04 | 0.04 | 0.04 | 0.04 | 0.04 | 0.04 |
| Perfume | 0.35 | 0.35 | 0.35 | 0.35 | 0.35 | 0.35 |
| Water | | | balance to 100% | | | |

Product pH is about 7.

In Examples 7–10 the Proteases #3 s 1–11 and 13–25 recited in Table III, among others including the additional proteases useful in the present invention described in Tables V and VI, are substituted for Protease #12, with substantially similar results.

In Examples 11 and 12, any combination of the protease enzymes useful in the present invention recited in Tables III, V and VI, among others, are substituted for Protease #12 and Protease #4, with substantially similar results.

2. Dishwashing Compositions

In another embodiment of the present invention, dishwashing compositions comprise one or more protease enzymes. As used herein, "dishwashing composition" refers to all forms for compositions for cleaning dishes, including but not limited to, granular and liquid forms. The dishwashing composition embodiment of the present invention is illustrated by the following examples.

EXAMPLES 13–18

Dishwashing Composition

| Component | _____ Example No. _____ | | | | | |
|---|---|---|---|---|---|---|
| | 13 | 14 | 15 | 16 | 17 | 18 |
| Protease #12 | 0.05 | 0.50 | 0.02 | 0.40 | 0.10 | 0.03 |
| Protease #4 | — | — | — | — | 0.40 | 0.02 |
| $C_{12}$–$C_{14}$ N-methyl-glucamide | 0.90 | 0.90 | 0.90 | 0.90 | 0.90 | 0.90 |
| $C_{12}$ ethoxy (1) sulfate | 12.00 | 12.00 | 12.00 | 12.00 | 12.00 | 12.00 |
| 2-methyl undecanoic acid | 4.50 | 4.50 | — | 4.50 | 4.50 | — |
| $C_{12}$ ethoxy (2) carboxylate | 4.50 | 4.50 | 4.50 | 4.50 | 4.50 | 4.50 |
| $C_{12}$ alcohol ethoxylate (4) | 3.00 | 3.00 | 3.00 | 3.00 | 3.00 | 3.00 |
| $C_{12}$ amine oxide | 3.00 | 3.00 | 3.00 | 3.00 | 3.00 | 3.00 |
| Sodium cumene sulfonate | 2.00 | 2.00 | 2.00 | 2.00 | 2.00 | 2.00 |
| Ethanol | 4.00 | 4.00 | 4.00 | 4.00 | 4.00 | 4.00 |
| $Mg^{++}$ (as $MgCl_2$) | 0.20 | 0.20 | 0.20 | 0.20 | 0.20 | 0.20 |
| $Ca^{++}$ (as $CaCl_2$) | 0.40 | 0.40 | 0.40 | 0.40 | 0.40 | 0.40 |
| Water | balance to 100% | | | | | |

Product pH is adjusted to 7.

In Examples 13–16 the Proteases #'s 1–11 and 13–25 recited in Table III, among others including the additional proteases useful in the present invention described in Tables V and VI, are substituted for Protease #12, with substantially similar results.

In Examples 17 and 18, any combination of the protease enzymes useful in the present invention recited in Tables III, V and VI, among others, are substituted for Protease #12 and Protease #4 with substantially similar results.

EXAMPLE 19

Granular Automatic Dishwashing Composition

| Component | A | B | C |
|---|---|---|---|
| Citric Acid | 15.0 | — | — |
| Citrate | 4.0 | 29.0 | 15.0 |
| Acrylate/methacrylate copolymer | 6.0 | — | 6.0 |
| Acrylic acid maleic acid copolymer | — | 3.7 | — |
| Dry add carbonate | 9.0 | — | 20.0 |
| Alkali metal silicate | 8.5 | 17.0 | 9.0 |
| Paraffin | — | 0.5 | — |
| Benzotriazole | — | 0.3 | — |
| Termamyl 60T | 1.5 | 1.5 | 1.0 |
| Protease #12 (4.6% prill) | 1.6 | 1.6 | 1.6 |
| Percarbonate (AvO) | 1.5 | — | — |
| Perborate monohydrate | — | 0.3 | 1.5 |
| Perborate tetrahydrate | — | 0.9 | — |
| Tetraacetylethylene diamine | 3.8 | 4.4 | — |
| Diethylene triamine penta methy phosphonic acid (Mg salt) | 0.13 | 0.13 | 0.13 |
| Alkyl ethoxy sulphate - 3 times ethoxylated | 3.0 | — | — |
| Alkyl ethoxy propoxy nonionic surfactant | — | 1.5 | — |
| Suds suppressor | 2.0 | — | — |
| Olin SLF18 nonionic surfactant | — | — | 2.0 |
| Sulphate | Balance to 100% | | |

In Examples 19 A–C the Protease #3 s 1–11 and 13–25 recited in Table III, among others including the additional proteases useful in the present invention described in Tables V and VI, are substituted for Protease #12, with substantially similar results. Also in Examples 19 A–C, any combination of the proteases useful in the present invention recited in Tables III, V and VI among others, are substituted for Protease #12 with substantially similar results.

3. Fabric cleaning compositions

In another embodiment of the present invention, fabric cleaning compositions comprise one or more protease enzymes. As used herein, "fabric cleaning composition" refers to all forms for detergent compositions for cleaning fabrics, including but not limited to, granular, liquid and bar forms.

a. Granular fabric cleaning compositions

The granular fabric cleaning compositions of the present invention contain an effective amount of one or more protease enzymes, preferably from about 0.001% to about 10%, more preferably from about 0.005% to about 5%, more preferably from about 0.01% to about 1% by weight of active protease enzyme of the composition. In addition to one or more protease enzymes, the granular fabric cleaning compositions typically comprise at least one surfactant, one or more builders, and, in some cases, a bleaching agent.

The granular fabric cleaning composition embodiment of the present invention is illustrated by the following examples.

EXAMPLES 20–23

Granular Fabric Cleaning Composition

| Component | _____ Example No. _____ | | | |
|---|---|---|---|---|
| | 20 | 21 | 22 | 23 |
| Protease #12 (4% Prill) | 0.10 | 0.20 | 0.03 | 0.05 |
| Protease #4 (4% Prill) | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 20–21 the Proteases #3 s 1–11 and 13–25 recited in Table III, among others including the additional proteases useful in the present invention described in Tables V and VI, are substituted for Protease #12, with substantially similar results.

In Examples 22 and 23, any combination of the protease enzymes useful in the present invention recited in Tables III, V and VI, among others, are substituted for Protease #12 and Protease #4, with substantially similar results.

EXAMPLES 24–27

Granular Fabric Cleaning Composition

| Component | _____ Example No. _____ | | | |
|---|---|---|---|---|
| | 24 | 25 | 26 | 27 |
| Protease #12 (4% Prill) | 0.10 | 0.20 | 0.03 | 0.05 |
| Protease #4 (4% Prill) | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Fillers, water, minors | balance to 100% | | | |

In Examples 24 and 25 the Proteases #3 s 1–11 and 13–25 recited in Table III, among others including the additional proteases useful in the present invention described in Tables V and VI, are substituted for Protease #12, with substantially similar results.

In Examples 26 and 27, any combination of the protease enzymes useful in the present invention recited in Tables III, V and VI, among others, are substituted for Protease #12 and Protease #4, with substantially similar results.

EXAMPLES 28 and 29

Granular Fabric Cleaning Compositions

| Components | Example No. 28 | Example No. 29 |
| --- | --- | --- |
| Linear alkyl benzene sulphonate | 11.4 | 10.70 |
| Tallow alkyl sulphate | 1.80 | 2.40 |
| $C_{14-15}$ alkyl sulphate | 3.00 | 3.10 |
| $C_{14-15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| Diethylene triamine penta methylene phosphonic acid | 1.00 | 0.20 |
| Protease #12 (4% Prill) | 0.30 | 0.30 |
| Lipase | 0.36 | 0.40 |
| Amylase | 0.30 | 0.30 |
| Sodium silicate | 2.00 | 2.50 |
| Sodium sulphate | 3.50 | 5.20 |
| Polyvinyl pyrrolidone | 0.30 | 0.50 |
| Perborate | 0.5 | 1 |
| Phenol sulphonate | 0.1 | 0.2 |
| Peroxidase | 0.1 | 0.1 |
| Minors | Up to 100 | Up to 100 |

EXAMPLES 30 and 31

Granular Fabric Cleaning Compositions

| Components | Example No. 30 | Example No. 31 |
| --- | --- | --- |
| Sodium linear $C_{12}$ alkyl benzene-sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Polyvinyl pyrrolidone | 0.5 | 0.7 |
| Tetraacetylethylene diamine | 3.0 | 3.0 |
| Boric acid | 4.0 | — |
| Perborate | 0.5 | 1 |
| Phenol sulphonate | 0.1 | 0.2 |
| Protease #12 (4% Prill) | 0.4 | 0.4 |
| Fillers (e.g., silicates; carbonates; perfumes; water) | Up to 100 | Up to 100 |

EXAMPLE 32

Compact Granular Fabric Cleaning Composition

| Components | Weight % |
| --- | --- |
| Alkyl Sulphate | 8.0 |
| Alkyl Ethoxy Sulphate | 2.0 |
| Mixture of C25 and C45 alcohol 3 and 7 times ethoxylated | 6.0 |
| Polyhydroxy fatty acid amide | 2.5 |
| Zeolite | 17.0 |
| Layered silicate/citrate | 16.0 |
| Carbonate | 7.0 |
| Maleic acid acrylic acid copolymer | 5.0 |
| Soil release polymer | 0.4 |
| Carboxymethyl cellulose | 0.4 |
| Poly(4-vinylpyridine)-N-oxide | 0.1 |
| Copolymer of vinylimidazole and vinylpyrrolidone | 0.1 |
| PEG2000 | 0.2 |
| Protease #12 (4% Prill) | 0.5 |
| Lipase | 0.2 |
| Cellulase | 0.2 |
| Tetracetylethylene diamine | 6.0 |
| Percarbonate | 22.0 |
| Ethylene diamine disuccinic acid | 0.3 |
| Suds suppressor | 3.5 |
| Disodium-4,4'-bis(2-morpholino-4-anilino-s-triazin-6-ylamino)stilbene-2,2'-disulphonate | 0.25 |
| Disodium-4,4'-bis(2-sulfostyril)biphenyl | 0.05 |
| Water, Perfume and Minors | Up to 100 |

EXAMPLE 33

Granular Fabric Cleaning Composition

| Component | Weight % |
| --- | --- |
| Linear alkyl benzene sulphonate | 7.6 |
| $C_{16}$–$C_{18}$ alkyl sulfate | 1.3 |
| $C_{14-15}$ alcohol 7 times ethoxyiated | 4.0 |
| Coco-alkyl-dimethyl hydroxyethyl ammonium chloride | 1.4 |
| Dispersant | 0.07 |
| Silicone fluid | 0.8 |
| Trisodium citrate | 5.0 |
| Zeolite 4A | 15.0 |
| Maleic acid acrylic acid copolymer | 4.0 |
| Diethylene triamine penta methylene phosphonic acid | 0.4 |
| Perborate | 15.0 |
| Tetraacetylethylene diamine | 5.0 |
| Smectite clay | 10.0 |
| Poly (oxy ethylene) (MW 300,000) | 0.3 |
| Protease #12 (4% Prill) | 0.4 |
| Lipase | 0.2 |
| Amylase | 0.3 |
| Cellulase | 0.2 |
| Sodium silicate | 3.0 |
| Sodium carbonate | 10.0 |
| Carboxymethyl cellulose | 0.2 |
| Brighteners | 0.2 |
| Water, perfume and minors | Up to 100 |

EXAMPLE 34

Granular Fabric Cleaning Composition

| Component | Weight % |
| --- | --- |
| Linear alkyl benzene sulfonate | 6.92 |
| Tallow alkyl sulfate | 2.05 |
| $C_{14-15}$ alcohol 7 times ethoxylated | 4.4 |
| $C_{12-15}$ alkyl ethoxy sulfate - 3 times ethoxylated | 0.16 |
| Zeolite | 20.2 |
| Citrate | 5.5 |
| Carbonate | 15.4 |
| Silicate | 3.0 |
| Maleic acid acrylic acid copolymer | 4.0 |
| Carboxymethyl cellulase | 0.31 |
| Soil release polymer | 0.30 |
| Protease #12 (4% Prill) | 0.2 |

Granular Fabric Cleaning Composition

| Component | Weight % |
|---|---|
| Lipase | 0.36 |
| Cellulase | 0.13 |
| Perborate tetrahydrate | 11.64 |
| Perborate monohydrate | 8.7 |
| Tetraacetylethylene diamine | 5.0 |
| Diethylene tramine penta methyl phosphonic acid | 0.38 |
| Magnesium sulfate | 0.40 |
| Brightener | 0.19 |
| Perfume, silicone, suds suppressors | 0.85 |
| Minors | Up to 100 |

In each of Examples 28–34 herein the Protease #'s 1–11 and 13–25 recited in Table III, among others including the additional proteases useful in the present invention described in Tables V and VI, are substituted for Protease #12, with substantially similar results. Also in Examples 28–34, any combination of the proteases useful in the present invention recited in Tables III, V and VI, among others, are substituted for Protease #12 with substantially similar results.

b. Liquid fabric cleaning compositions

Liquid fabric cleaning compositions of the present invention comprise an effective amount of one or more protease enzymes, preferably from about 0.0001% to about 10%, more preferably from about 0.001% to about 1%, and most preferably from about 0.001% to about 0.1%, by weight of active protease enzyme of the composition. Such liquid fabric cleaning compositions typically additionally comprise an anionic surfactant, a fatty acid, a water-soluble detergency builder and water.

The liquid fabric cleaning composition embodiment of the present invention is illustrated by the following examples.

EXAMPLES 35–39

Liquid Fabric Cleaning Compositions

| Component | 35 | 36 | 37 | 38 | 39 |
|---|---|---|---|---|---|
| Protease #12 | 0.05 | 0.03 | 0.30 | 0.03 | 0.10 |
| Protease #4 | — | — | — | 0.01 | 0.20 |
| $C_{12}$–$C_{14}$ alkyl sulfate, Na | 20.00 | 20.00 | 20.00 | 20.00 | 20.00 |
| 2-Butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In Examples 35–37 the Proteases #'s 1–11 and 13–25 recited in Table III, among others including the additional proteases useful in the present invention described in Tables V and VI, are substituted for Protease #12, with substantially similar results.

In Examples 38 and 39, any combination of the protease enzymes useful in the present invention recited in Tables III, V and VI, among others, are substituted for Protease #12 and Protease #4, with substantially similar results.

EXAMPLES 40–41

Liquid Fabric Cleaning Compositions

| Component | 40 | 41 |
|---|---|---|
| $C_{12–14}$ alkenyl succinic acid | 3.0 | 8.0 |
| Citric acid monohydrate | 10.0 | 15.0 |
| Sodium $C_{12–15}$ alkyl sulphate | 8.0 | 8.0 |
| Sodium sulfate of $C_{12–15}$ alcohol 2 times ethoxylated | — | 3.0 |
| $C_{12–15}$ alcohol 7 times ethoxylated | — | 8.0 |
| $C_{12–15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Protease #12 | 0.2 | 0.2 |
| Polyvinyl pyrrolidone | 1.0 | 2.0 |
| Suds suppressor | 0.15 | 0.15 |
| NaOH | up to pH 7.5 | |
| Perborate | 0.5 | 1 |
| Phenol sulphonate | 0.1 | 0.2 |
| Peroxidase | 0.4 | 0.1 |
| Waters and minors | up to 100 parts | |

In each of Examples 40 and 41 herein the Protease #'s 1–11 and 13–25 recited in Table III, among others including the additional proteases useful in the present invention described in Tables V and VI, are substituted for Protease #12, with substantially similar results. Also in Examples 40 and 41, any combination of the proteases useful in the present invention recited in Tables III, V and VI, among others, are substituted from Protease #12 with substantially similar results.

c. Bar fabric cleaning compositions

Bar fabric cleaning compositions of the present invention suitable for hand-washing soiled fabrics contain an effective amount of one or more protease enzymes, preferably from about 0.001% to about 10%, more preferably from about 0.01% to about 1% by weight of the composition.

The bar fabric cleaning composition embodiment of the present invention is illustrated by the following examples.

EXAMPLES 42–45

Bar Fabric Cleaning Compositions

| Component | 42 | 43 | 44 | 45 |
|---|---|---|---|---|
| Protease #12 | 0.3 | — | 0.1 | 0.02 |
| Protease #4 | — | — | 0.4 | 0.03 |
| $C_{12}$–$C_{16}$ alkyl sulfate, Na | 20.0 | 20.0 | 20.0 | 20.00 |
| $C_{12}$–$C_{14}$ N-methyl glucamide | 5.0 | 5.0 | 5.0 | 5.00 |
| $C_{11}$–$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10µ) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

In Examples 42 and 43 the Proteases #'s 1–11 and 13–25 recited in Table III, among others including the additional proteases useful in the present invention described in Tables V and VI, are substituted for Protease #12, with substantially similar results.

In Examples 44 and 45, any combination of the protease enzymes useful in the present invention recited in Tables III, V and VI, among others, are substituted for Protease #12 and Protease #4, with substantially similar results.

B. Additional Cleaning Compositions

In addition to the hard surface cleaning, dishwashing and fabric cleaning compositions discussed above, one or more protease enzymes may be incorporated into a variety of other cleaning compositions where hydrolysis of an insoluble substrate is desired. Such additional cleaning compositions include but am not limited to, oral cleaning compositions, denture cleaning compositions, and contact lens cleaning compositions.

1. Oral cleaning compositions

In another embodiment of the present invention, a pharmaceutically-acceptable amount of one or more protease enzymes are included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, oral cleaning compositions of the present invention comprise from about 0.0001% to about 20% of one or more protease enzymes, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in U.S. Pat. No. 5,096,700, Seibel, issued Mar. 17, 1992; U.S. Pat. No. 5,028,414, Sampathkumar, issued Jul. 2, 1991; and U.S. Pat. No. 5,028,415, Benedict, Bush and Sunberg, issued Jul. 2, 1991; all of which are incorporated herein by reference.

The oral cleaning composition embodiment of the present invention is illustrated by the following examples.

EXAMPLES 46–49

| Dentifrice Composition | | | | |
|---|---|---|---|---|
| | Example No. | | | |
| Component | 46 | 47 | 48 | 49 |
| Protease #12 | 2.000 | 3.500 | 1.500 | 2.000 |
| Sorbitol (70% aqueous solution) | 35.000 | 35.000 | 35.000 | 35.000 |
| PEG-6* | 1.000 | 1.000 | 1.000 | 1.000 |
| Silica dental abrasive** | 20.000 | 20.000 | 20.000 | 20.000 |
| Sodium fluoride | 0.243 | 0.243 | 0.243 | 0.243 |
| Titanium dioxide | 0.500 | 0.500 | 0.500 | 0.500 |
| Sodium saccharin | 0.286 | 0.286 | 0.286 | 0.286 |
| Sodium alkyl sulfate (27.9% aqueous solution) | 4.000 | 4.000 | 4.000 | 4.000 |
| Flavor | 1.040 | 1.040 | 1.040 | 1.040 |
| Carboxyvinyl Polymer*** | 0.300 | 0.300 | 0.300 | 0.300 |
| Carrageenan**** | 0.800 | 0.800 | 0.800 | 0.800 |
| Water | balance to 100% | | | |

*PEG-6 = Polyethylene glycol having a molecular weight of 600.
**Precipitated silica identified as Zeodent 119 offered by J. M. Huber.
***Carbopol offered by B. F. Goodrich Chemical Company.
****Iota Carrageenan offered by Hercules Chemical Company.

In Examples 46–49 the Proteases #'s 1–11 and 13–25 recited in Table III, among others including the additional proteases useful in the present invention described in Tables V and VI, are substituted for Protease #12, with substantially similar results. Also in Examples 46–49, any combination of the protease enzymes useful in the present invention recited in Tables III, V, VI, among others, are substituted for Protease #12 with substantially similar results.

EXAMPLES 50–53

| Mouthwash Composition | | | | |
|---|---|---|---|---|
| | Example No. | | | |
| Component | 50 | 51 | 52 | 53 |
| Protease #12 | 3.00 | 7.50 | 1.00 | 5.00 |
| SDA 40 Alcohol | 8.00 | 8.00 | 8.00 | 8.00 |
| Flavor | 0.08 | 0.08 | 0.08 | 0.08 |
| Emulsifier | 0.08 | 0.08 | 0.08 | 0.08 |
| Sodium Fluoride | 0.05 | 0.05 | 0.05 | 0.05 |
| Glycerin | 10.00 | 10.00 | 10.00 | 10.00 |
| Sweetener | 0.02 | 0.02 | 0.02 | 0.02 |
| Benzoic acid | 0.05 | 0.05 | 0.05 | 0.05 |
| Sodium hydroxide | 0.20 | 0.20 | 0.20 | 0.20 |
| Dye | 0.04 | 0.04 | 0.04 | 0.04 |
| Water | balance to 100% | | | |

In Examples 50–53 the Proteases #'s 1–11 and 13–25 recited in Table III, among others including the additional proteases useful in the present invention described in Tables V and VI, are substituted for Protease #12, with substantially similar results. Also in Examples 50–53, any combination of the protease enzymes useful in the present invention recited in Tables III, V, and VI, among others, are substituted for Protease #12 with substantially similar results.

EXAMPLES 54–57

Lozenge Composition

| Component | _____ Example No. _____ | | | |
|---|---|---|---|---|
| | 54 | 55 | 56 | 57 |
| Protease #12 | 0.01 | 0.03 | 0.10 | 0.02 |
| Sorbitol | 17.50 | 17.50 | 17.50 | 17.50 |
| Mannitol | 17.50 | 17.50 | 17.50 | 17.50 |
| Starch | 13.60 | 13.60 | 13.60 | 13.60 |
| Sweetener | 1.20 | 1.20 | 1.20 | 1.20 |
| Flavor | 11.70 | 11.70 | 11.70 | 11.70 |
| Color | 0.10 | 0.10 | 0.10 | 0.10 |
| Corn Syrup | balance to 100% | | | |

In Examples 54–57 the Proteases #'s 1–11 and 13–25 recited in Table III, among others including the additional proteases useful in the present invention described in Tables V and VI, are substituted for Protease #12, with substantially similar results. Also in Examples 54–57, any combination of the protease enzymes useful in the present invention recited in Tables III, V and VI, among others, are substituted for Protease #12 with substantially similar results.

EXAMPLES 58–61

Chewing Gum Composition

| Component | _____ Example No. _____ | | | |
|---|---|---|---|---|
| | 58 | 59 | 60 | 61 |
| Protease #12 | 0.03 | 0.02 | 0.10 | 0.05 |
| Sorbitol crystals | 38.44 | 38.40 | 38.40 | 38.40 |
| Paloja-T gum base* | 20.00 | 20.00 | 20.00 | 20.00 |
| Sorbitol (70% aqueous solution) | 22.0 | 22.00 | 22.00 | 22.00 |
| Mannitol | 10.00 | 10.00 | 10.00 | 10.00 |
| Glycerine | 7.56 | 7.56 | 7.56 | 7.56 |
| Flavor | 1.00 | 1.00 | 1.00 | 1.00 |

*Supplied by L.A. Dreyfus Company.

In Examples 58–61 the Proteases #'s 1–11 and 13–25 recited in Table III, among others including the additional proteases useful in the present invention described in Tables V and VI, are substituted for Protease #12, with substantially similar results. Also in Examples 58–61, any combination of the protease enzymes useful in the present invention recited in Tables III, V, and VI, among others, are substituted for Protease #12 with substantially similar results.

2. Denture cleaning compositions

In another embodiment of the present invention, denture cleaning compositions for cleaning dentures outside of the oral cavity comprise one or more protease enzymes. Such denture cleaning compositions comprise an effective amount of one or more protease enzymes, preferably from about 0.0001% to about 50% of one or more protease enzymes, more preferably from about 0.001% to about 35%, more preferably still from about 0.01% to about 20%, by weight of the composition, and a denture cleansing carrier. Various denture cleansing composition formats such as effervescent tablets and the like are well known in the art (see for example U.S. Pat. No. 5,055,305, Young, incorporated herein by reference), and are generally appropriate for incorporation of one or more protease enzymes for removing proteinaceous stains from dentures.

The denture cleaning composition embodiment of the present invention is illustrated by the following examples.

EXAMPLES 62–65

Two-layer Effervescent Denture Cleansing Tablet

| Component | _____ Example No. _____ | | | |
|---|---|---|---|---|
| | 62 | 63 | 64 | 65 |
| Acidic Layer | | | | |
| Protease #12 | 1.0 | 1.5 | 0.01 | 0.05 |
| Tartaric acid | 24.0 | 24.0 | 24.00 | 24.00 |
| Sodium carbonate | 4.0 | 4.0 | 4.00 | 4.00 |
| Sulphamic acid | 10.0 | 10.0 | 10.00 | 10.00 |
| PEG 20,000 | 4.0 | 4.0 | 4.00 | 4.00 |
| Sodium bicarbonate | 24.5 | 24.5 | 24.50 | 24.50 |
| Potassium persulfate | 15.0 | 15.0 | 15.00 | 15.00 |
| Sodium acid pyrophosphate | 7.0 | 7.0 | 7.00 | 7.00 |
| Pyrogenic silica | 2.0 | 2.0 | 2.00 | 2.00 |
| Tetracetylethylene diamine | 7.0 | 7.0 | 7.00 | 7.00 |
| Ricinoleylsulfosuccinate | 0.5 | 0.5 | 0.50 | 0.50 |
| Flavor | 1.0 | 1.0 | 1.00 | 1.00 |
| Alkaline Layer | | | | |
| Sodium perborate monohydrate | 32.0 | 32.0 | 32.00 | 32.00 |
| Sodium bicarbonate | 19.0 | 19.0 | 19.00 | 19.00 |
| EDTA | 3.0 | 3.0 | 3.00 | 3.00 |
| Sodium tripolyphosphate | 12.0 | 12.0 | 12.00 | 12.00 |
| PEG 20,000 | 2.0 | 2.0 | 2.00 | 2.00 |
| Potassium persulfate | 26.0 | 26.0 | 26.00 | 26.00 |
| Sodium carbonate | 2.0 | 2.0 | 2.00 | 2.00 |
| Pyrogenic silica | 2.0 | 2.0 | 2.00 | 2.00 |
| Dye/flavor | 2.0 | 2.0 | 2.00 | 2.00 |

In Examples 62–65 the Proteases #'s 1–11 and 13–25 recited in Table III, among others including the additional proteases useful in the present invention described in Tables V and VI, are substituted for Protease #12, with substantially similar results. Also in Examples 62–65, any combination of the protease enzymes useful in the present invention recited in Tables III, V and VI, among others, are substituted for Protease #12 with substantially similar results.

3. Personal Cleansing Compositions

In another embodiment of the present invention, personal cleaning compositions for cleaning the skin (in liquid and bar form) comprise one or more of the protease enzymes. Such compositions typically comprise from about 0.001% to about 5% protease enzyme, preferably from about 0.005% to about 2%, and most preferably from about 0.01% to about 0.8% by weight of the composition. Preferred personal cleansing compositions into which can be included protease enzymes as described herein are taught in U.S. patent applications Ser. No. 08/121,623 and Ser. No. 08/121,624, both by Visscher et al., filed Sept. 14, 1993, the disclosures of which are incorporated herein by reference in their entirety. Such compositions are illustrated by the following examples.

EXAMPLE 66

Liquid Personal Cleansing Compositions Containing Soap

| Component | Weight % |
|---|---|
| Soap (K or Na) | 15.00 |
| 30% Laurate | |
| 30% Myristate | |
| 25% Palmitate | |
| 15% Stearate | |
| Fatty acids (above ratios) | 4.50 |
| Na Lauryl Sarcosinate | 6.00 |

-continued

| Liquid Personal Cleansing Compositions Containing Soap | |
|---|---|
| Component | Weight % |
| Sodium Laureth-3 Sulfate | 0.66 |
| Cocamidopropylbetaine | 1.33 |
| Glycerine | 15.00 |
| Propylene glycol | 9.00 |
| Polyquaternium 10 | 0.80 |
| Ethylene glycol distearate (EDTA) | 1.50 |
| Propylparaben | 0.10 |
| Methylparaben | 0.20 |
| Protease #12 | 0.10 |
| KOH or NaOH | If necessary to adjust pH |
| Calcium sulfate | 3 |
| Acetic acid | 3 |
| Water | Balance to 100 |

EXAMPLE 67

| Personal Cleansing Bar Composition | |
|---|---|
| Component | Weight % |
| Sodium Cocoyl Isethionate | 47.20 |
| Sodium Cetearyl Sulfate | 9.14 |
| Paraffin | 9.05 |
| Sodium Soap (in situ) | 3.67 |
| Sodium Isethionate | 5.51 |
| Sodium Chloride | 0.45 |
| Titanium Dioxide | 0.4 |
| Trisodium EDTA | 0.1 |
| Trisodium Etidronate | 0.1 |
| Perfume | 1.20 |
| $Na_2SO_4$ | 0.87 |
| Protease #12 | 0.10 |
| Water/Minors | Balance to 100 |

In Examples 66–67 the Proteases #3 s 1–11 and 13–25 recited in Table III, among others including the additional proteases useful in the present invention described in Tables V and VI, are substituted for Protease #12, with substantially similar results. Also in Examples 66–67, any combination of the protease enzymes useful in the present invention recited in Tables III, V, and VI, among others, are substituted for Protease #12 with substantially similar results.

EXAMPLE 68

Wash Performance Test

The wash performance of the variants useful in the present invention compositions is evaluated by measuring the removal of stain from EMPA 116(blood/milk/carbon black on cotton) cloth swatches (Testfabrics, Inc., Middlesex, N.J. 07030).

Six EMPA 116 swatches, cut to 3×4½ inches with pinked edges, are placed in each pot of a Model 7243S Terg-O-Tometer (United States Testing Co., Inc., Hoboken, N.J.) containing 1000 ml of water, 15 gpg hardness (Ca++:Mg++::3:1::w:w), 7 g of detergent, and enzyme as appropriate. The detergent base is WFK1 detergent from wfk— Testgewebe GmbH, Adlerstrasse 42, Postfach 13 07 62, D-47759 Krefeld, Germany:

| Component | % of Final Formulation |
|---|---|
| Zeolite A | 25% |
| Sodium sulfate | 25% |
| Soda Ash | 10% |
| Linear alkylbenzenesulfonate | 8.8% |
| Alcohol ethoxylate (7–8 EO) | 4.5% |
| Sodium soap | 3% |
| Sodium silicate ($SiO_2:Na_2O::3.3:1$) | 3% |

To this base detergent, the following additions are made:

| Component | % of Final Formulation |
|---|---|
| Sodium perborate monohydrate | 13% |
| Copolymer (Sokalan CP5) | 4% |
| TAED (Mykon ATC Green) | 3% |
| Enzyme | 0.5% |
| Brightener (Tinopal AMS-GX) | 0.2% |

Sodium perborate monohydrate is obtained from Degussa Corporation, Ridgefield-Park, N.J. 07660. Sokalan CP5 is obtained from BASF Corporation, Parsippany, N.J. 07054. Mykon ATC Green (TAED, tetraacetylethylenediamine) is obtained from Warwick International, Limited, Mostyn, Holywell, Clwyd CH8 9HE, England. Tinopal AMS GX is obtained from Ciba-Geigy Corporation, Greensboro, N.C. 27419.

Six EMPA 116 swatches are washed in detergent with enzyme for 30min at 60° C. and are subsequently rinsed twice for 5 minutes each time in 1000 ml water. Enzymes are added at final concentrations of 0.05 to 1 ppm for standard curves, and 0.25 ppm for routine analyses. Swatches are dried and pressed, and the reflectance from the swatches is measured using the L value on the L*a*b* scale of a Minolta Chroma Meter, Model CR-200 (Minolta Corporation, Ramsey, N.J. 07446). Performance is reported as a percentage of the performance of B. lentus (GG36) protease and is calculated by dividing the amount of B. lentus (GG36) protease by the amount of variant protease that is needed to provide the same stain removal performance×100. The data are shown in Table VII.

TABLE VII

| Enzyme | Wash Performance |
|---|---|
| B. lentus subtilisin | 100 |
| N76D | 310 |
| N76D/S103A | 230 |
| N76D/V104I | 130 |
| N76D/V107V | 160 |
| N76D/S99D/S101R | 370 |
| N76D/S99D/S103A | 290 |
| N76D/S101R/S103A | 130 |
| N76D/S101R/V104I | 300 |
| N76D/S103A/V104I | 320 |
| N76D/S103G/V104I | 160 |
| N76D/S103A/V104F | 210 |
| N76D/S103A/V104N | 110 |
| N76D/S103A/V104T | 170 |
| N76D/V104I/I107V | 210 |
| N76D/S99D/S101R/S103A | 220 |
| N76D/S99D/S101R/V104I | 140 |
| N76D/S101G/S103A/V104I | 170 |
| N76D/S101R/S103A/V104I | 150 |
| N76D/S103A/V104I/S105A | 170 |
| N76D/S103A/V104T/I107A | 120 |
| N76D/S103A/V104T/I107L | 110 |
| N76D/S013A/V104I/L126F | 110 |
| N76D/S103A/V104I/S128G | 280 |

TABLE VII-continued

| Enzyme | Wash Performance |
| --- | --- |
| N76D/S103A/V104I/L135I | 160 |
| N76D/S103A/V104I/L135V | 160 |
| N76D/S103A/V104I/D197E | 170 |
| N76D/S103A/V104I/N204A | 160 |
| N76D/S103A/V104I/N204G | 150 |
| N76D/S103A/V104I/P210I | 470 |
| N76D/S103A/V104I/M222A | 100 |
| N76D/S103A/V104I/T260P | 280 |
| N76D/S103A/V104I/S265N | 190 |

EXAMPLES 69

Protease Stability in a Liquid Detergent Formulation

Figure 10:
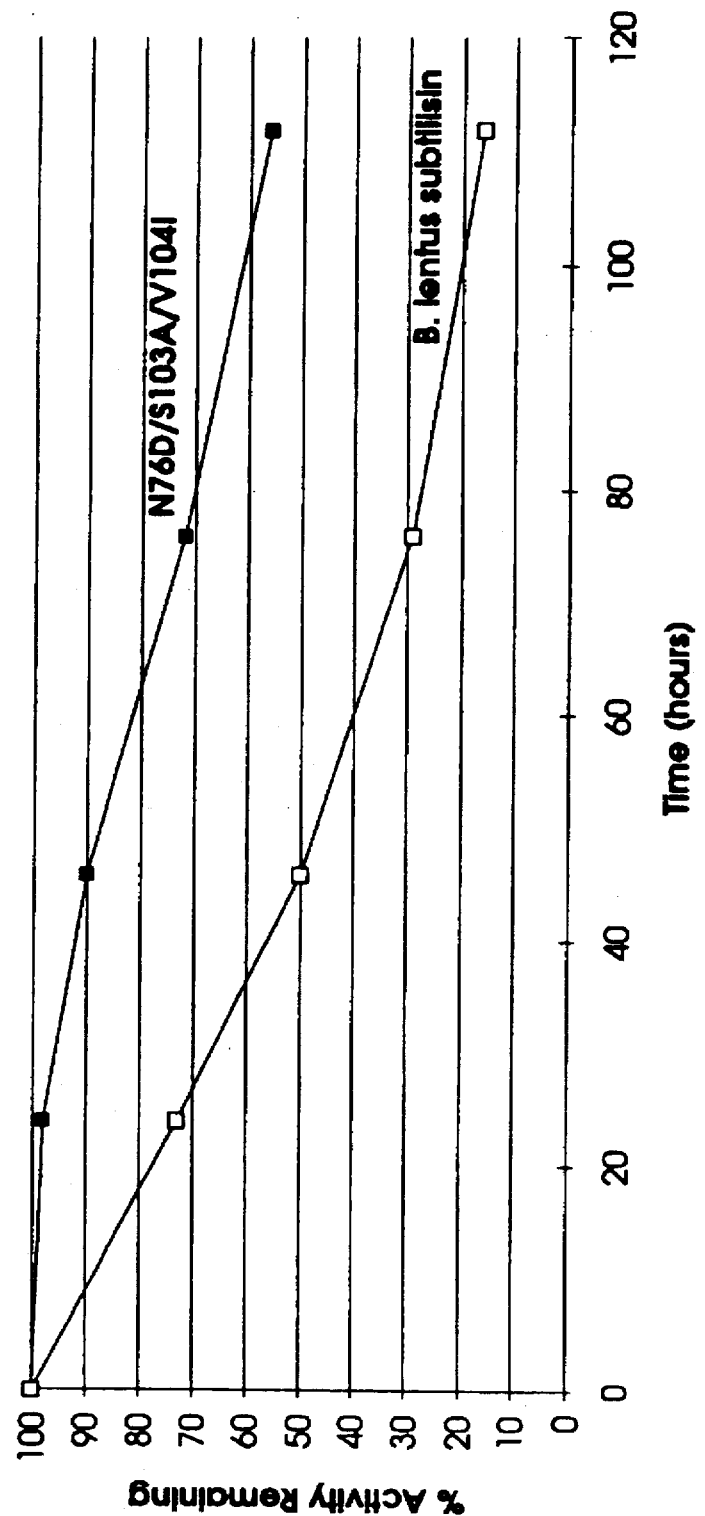
FIG. 10 shows the stability of a preferred mutant enzyme compared to wild-type, in a liquid detergent formulation.

A comparison of protease stability toward inactivation in a liquid detergent formulation is made for *Bacillus lentus* subtilisin and its variant enzyme N76D/S103A/V104I according to the procedure outlined herein. The detergent formulation for the study is a commercially purchased bottle of Tide Ultra liquid laundry detergent made in the USA by The Proctor & Gamble Company. Heat treatment of the detergent formulation is necessary to inactivate in-situ protease. This is accomplished by incubating the detergent at 96° C. for a period of 4.5 hours. Concentrated preparations of the *B. lentus* subtilisin and N76D/S103A/V104I variant, in the range of 20 grams/liter enzyme, are then added to the heat-treated Tide Ultra at room-temperature to a final concentratrion of 0.3 grams/liter enzyme in the detergent formulation. The heat-treated detergent with protease added is then incubated in a water bath thermostatted at 50° C. Aliquots are removed from the incubation tubes at 0, 24, 46, 76, and 112 hour time intervals and assayed for enzyme activity by addition to a 1 cm cuvette containing 1.2 mM of the synthetic peptide substrate suc-Ala-Ala-Pro-phe-p-nitroanilide dissolved in 0.1M tris-HCL buffer, pH 8.6, and thermostatted at 25° C. The initial linear reaction velocity is followed spectrophotometrically by monitoring the absorbance of the reaction product p-nitroaniline at 410 nm as a function of time. As shown in FIG. 10, the N76D/S103A/V104I variant is observed to have significantly greater stability towards inactivation than the native *B. lentus* enzyme. Estimated half-lives for inactivation in the Tide Ultra detergent formulation for the two enzymes, under the specified test conditions, are 45 hours for *B. lentus* subtilisin and 125 hours for the N76D/S103A/V104I variant.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

---

What is claimed is:

1. A fabric cleaning composition comprising:
   (a) from about 0.0001% to about 10% protease enzyme which is an N76D/S103A/V104I subtilisin variant derived from *Bacillus lentus* subtilisin;
   (b) at least about 5% surfactant;
   (c) at least about 5% builder; and
   (d) optionally, one or more cleaning composition materials compatible with the protease enzyme selected from the group consisting of solvents, buffers, enzymes, soil release agents, clay soil removal agents, dispersing agents, brighteners, suds suppressors, fabric softeners, suds boosters, enzyme stabilizers, bleaching agents, dyes, and perfumes.

2. The fabric cleaning composition according to claim 1 wherein the surfactant is selected from the group consisting of alkyl benzene sulfonates, primary alkyl sulfates, secondary alkyl sulfates, alkyl alkoxy sulfates, alkyl alkoxy carboxylates, alkyl polyglycides and their corresponding sulfated polyglycosides, alpha-sulfonate fatty esters, alkyl and alkyl phenol alkoxylates, betaines and sulfobetaines, amine oxides, N-methyl glucamides, nonionic primary alcohol ethoxylates, nonionic primary alcohol mixed ethoxy/propoxy, and mixtures thereof; and wherein further the builder is selected from the group consisting of zeolites, polycarboxylates, layered silicates, phosphates, and mixtures thereof.

3. The fabric cleaning composition according to claim 2 further comprising one or more cleaning composition materials selected from the group consisting of bleaching agents, fabric softeners, and enzymes.

4. The fabric cleaning composition according to claim 1 in the form of a concentrated granular fabric cleaning composition comprising at least about 30% surfactant.

5. A dishwashing composition comprising:
   (a) from about 0.0001% to about 10% protease enzyme which is an N76D/S103A/V104I subtilisin variant derived from *Bacillus lentus* subtilisin;
   (b) from about 0.1% to about 10% surfactant; and
   (c) optionally, one or more cleaning composition materials compatible with the protease enzyme selected from the group consisting of solvents, buffers, enzymes, dispersing agents, suds suppressors, enzyme stabilizers, bleaching agents, dyes, and perfumes.

6. A method for cleaning fabric, said method comprising contacting a fabric in need of cleaning with a protease enzyme which is an N76D/S103A/V104I subtilisin variant derived from *Bacillus lentus* subtilisin.

7. A method for cleaning dishes, said method comprising contacting a dish in need of cleaning with a protease enzyme which is an N76D/S103A/V104I subtilisin variant derived from *Bacillus lentus* subtilisin.

\* \* \* \* \*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GAAGCTGCAA CTCGTTAAA                  19

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCTGCTCTAG ACAATTCG                  18

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:3:

GTATTAGGGG CGGACGGTCG AGGCGCCATC AGCTCGATT         39

( 2 ) INFORMATION FOR SEQ ID NO:4:

( i ) SEQUENCE CHARACTERISTICS:
      ( A ) LENGTH: 33 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:4:

TCAGGTTCGG TCTCGAGCGT TGCCCAAGGA TTG         33

( 2 ) INFORMATION FOR SEQ ID NO:5:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

CACGTTGCTA GCTTGAGTTT AG         22

( 2 ) INFORMATION FOR SEQ ID NO:6:

( i ) SEQUENCE CHARACTERISTICS:
      ( A ) LENGTH: 1497 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:6:

```
GGTCTACTAA AATATTATTC CATACTATAC AATTAATACA CAGAATAATC TGTCTATTGG    60
TTATTCTGCA AATGAAAAAA AGGAGAGGAT AAAGAGTGAG AGGCAAAAAA GTATGGATCA   120
GTTGCTGTT  TGCTTTAGCG TTAATCTTTA CGATGGCGTT CGGCAGCACA TCCTCTGCCC   180
AGGCGGCAGG GAAATCAAAC GGGGAAAAGA AATATATTGT CGGGTTTAAA CAGACAATGA   240
GCACGATGAG CGCCGCTAAG AAGAAAGATG TCATTTCTGA AAAAGGCGGG AAAGTGCAAA   300
AGCAATTCAA ATATGTAGAC GCAGCTTCAG TCACATTAAA CGAAAAAGCT GTAAAAGAAT   360
TGAAAAAAGA CCCGAGCGTC GCTTACGTTG AAGAAGATCA CGTAGCACAT GCGTACGCGC   420
AGTCCGTGCC TTACGGCGTA TCACAAATTA AAGCCCCTGC TCTGCACTCT CAAGGCTACA   480
CTGGATCAAA TGTTAAAGTA GCGGTTATCG ACAGCGGTAT CGATTCTTCT CATCCTGATT   540
TAAAGGTAGC AAGCGGAGCC AGCATGGTTC CTTCTGAAAC AAATCCTTTC CAAGACAACA   600
ACTCTCACGG AACTCACGTT GCCGGCACAG TTGCGGCTCT TAATAACTCA ATCGGTGTAT   660
TAGGCGTTGC GCCAAGCGCA TCACTTTACG CTGTAAAAGT TCTCGGTGCT GACGGTTCCG   720
GCCAATACAG CTGGATCATT AACGGAATCG AGTGGGCGAT CGCAAACAAT ATGGACGTTA   780
TTAACATGAG CCTCGGCGGA CCTTCTGGTT CTGCTGCTTT AAAAGCGGCA GTTGATAAAG   840
CCGTTGCATC CGGCGTCGTA GTCGTTGCGG CAGCCGGTAA CGAAGGCACT TCCGGCAGCT   900
```

```
CAAGCACAGT GGGCTACCCT GGTAAATACC CTTCTGTCAT TGCAGTAGGC GCTGTTGACA        960
GCAGCAACCA AAGAGCATCT TTCTCAAGCG TAGGACCTGA GCTTGATGTC ATGGCACCTG       1020
GCGTATCTAT CCAAAGCACG CTTCCTGGAA ACAAATACGG GGCGTACAAC GGTACGTCAA       1080
TGGCATCTCC GCACGTTGCC GGAGCGGCTG CTTTGATTCT TTCTAAGCAC CCGAACTGGA       1140
CAAACACTCA AGTCCGCAGC AGTTTAGAAA ACACCACTAC AAAACTTGGT GATTCTTTGT       1200
ACTATGGAAA AGGGCTGATC AACGTACAAG CGGCAGCTCA GTAAAACATA AAAACCGGC        1260
CTTGGCCCCG CCGGTTTTTT ATTATTTTTC TTCCTCCGCA TGTTCAATCC GCTCCATAAT       1320
CGACGGATGG CTCCCTCTGA AAATTTAAC GAGAAACGGC GGGTTGACCC GGCTCAGTCC        1380
CGTAACGGCC AACTCCTGAA ACGTCTCAAT CGCCGCTTCC CGGTTTCCGG TCAGCTCAAT       1440
GCCATAACGG TCGGCGGCGT TTTCCTGATA CCGGGAGACG GCATTCGTAA TCGGATC         1497
```

( 2 ) INFORMATION FOR SEQ ID NO:7:

( i ) SEQUENCE CHARACTERISTICS:
        ( A ) LENGTH: 275 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Ala Gln Ser Val Pro Tyr Gly Val Ser Gln Ile Lys Ala Pro Ala Leu
  1           5                  10                  15

His Ser Gln Gly Tyr Thr Gly Ser Asn Val Lys Val Ala Val Ile Asp
             20                  25                  30

Ser Gly Ile Asp Ser Ser His Pro Asp Leu Lys Val Ala Gly Gly Ala
         35                  40                  45

Ser Met Val Pro Ser Glu Thr Asn Pro Phe Gln Asp Asn Asn Ser His
     50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                     85                  90                  95

Gly Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
```

|     |     |     |     | 245 |     |     |     |     | 250 |     |     |     |     | 255 |
| --- | --- | --- | --- | --- | --- | --- | --- | --- | --- | --- | --- | --- | --- | --- |
| Leu | Gly | Asp | Ser | Phe | Tyr | Tyr | Gly | Lys | Gly | Leu | Ile | Asn | Val | Gln | Ala |
|     |     |     | 260 |     |     |     |     | 265 |     |     |     | 270 |     |     |
| Ala | Ala | Gln |     |     |     |     |     |     |     |     |     |     |     |     |
|     |     | 275 |     |     |     |     |     |     |     |     |     |     |     |     |

( 2 ) INFORMATION FOR SEQ ID NO:8:

( i ) SEQUENCE CHARACTERISTICS:
  ( A ) LENGTH: 275 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:8:

| Ala | Gln | Ser | Val | Pro | Tyr | Gly | Ile | Ser | Gln | Ile | Lys | Ala | Pro | Ala | Leu |
| --- | --- | --- | --- | --- | --- | --- | --- | --- | --- | --- | --- | --- | --- | --- | --- |
| 1 |   |   |   | 5 |   |   |   |   | 10 |   |   |   |   | 15 |   |
| His | Ser | Gln | Gly | Tyr | Thr | Gly | Ser | Asn | Val | Lys | Val | Ala | Val | Ile | Asp |
|   |   |   | 20 |   |   |   |   | 25 |   |   |   |   | 30 |   |   |
| Ser | Gly | Ile | Asp | Ser | Ser | His | Pro | Asp | Leu | Asn | Val | Arg | Gly | Gly | Ala |
|   |   | 35 |   |   |   |   | 40 |   |   |   |   | 45 |   |   |   |
| Ser | Phe | Val | Pro | Ser | Glu | Thr | Asn | Pro | Tyr | Gln | Asp | Gly | Ser | Ser | His |
|   | 50 |   |   |   |   | 55 |   |   |   |   | 60 |   |   |   |   |
| Gly | Thr | His | Val | Ala | Gly | Thr | Ile | Ala | Ala | Leu | Asn | Asn | Ser | Ile | Gly |
| 65 |   |   |   |   | 70 |   |   |   |   | 75 |   |   |   |   | 80 |
| Val | Leu | Gly | Val | Ser | Pro | Ser | Ala | Ser | Leu | Tyr | Ala | Val | Lys | Val | Leu |
|   |   |   |   | 85 |   |   |   |   | 90 |   |   |   |   | 95 |   |
| Asp | Ser | Thr | Gly | Ser | Gly | Gln | Tyr | Ser | Trp | Ile | Ile | Asn | Gly | Ile | Glu |
|   |   |   | 100 |   |   |   |   | 105 |   |   |   |   | 110 |   |   |
| Trp | Ala | Ile | Ser | Asn | Asn | Met | Asp | Val | Ile | Asn | Met | Ser | Leu | Gly | Gly |
|   |   | 115 |   |   |   |   | 120 |   |   |   |   | 125 |   |   |   |
| Pro | Thr | Gly | Ser | Thr | Ala | Leu | Lys | Thr | Val | Val | Asp | Lys | Ala | Val | Ser |
|   | 130 |   |   |   |   | 135 |   |   |   |   | 140 |   |   |   |   |
| Ser | Gly | Ile | Val | Val | Ala | Ala | Ala | Ala | Gly | Asn | Glu | Gly | Ser | Ser | Gly |
| 145 |   |   |   |   | 150 |   |   |   |   | 155 |   |   |   |   | 160 |
| Ser | Thr | Ser | Thr | Val | Gly | Tyr | Pro | Ala | Lys | Tyr | Pro | Ser | Thr | Ile | Ala |
|   |   |   |   | 165 |   |   |   |   | 170 |   |   |   |   | 175 |   |
| Val | Gly | Ala | Val | Asn | Ser | Ser | Asn | Gln | Arg | Ala | Ser | Phe | Ser | Ser | Ala |
|   |   |   | 180 |   |   |   |   | 185 |   |   |   |   | 190 |   |   |
| Gly | Ser | Glu | Leu | Asp | Val | Met | Ala | Pro | Gly | Val | Ser | Ile | Gln | Ser | Thr |
|   |   | 195 |   |   |   |   | 200 |   |   |   |   | 205 |   |   |   |
| Leu | Pro | Gly | Gly | Thr | Tyr | Gly | Ala | Tyr | Asn | Gly | Thr | Ser | Met | Ala | Thr |
|   | 210 |   |   |   |   | 215 |   |   |   |   | 220 |   |   |   |   |
| Pro | His | Val | Ala | Gly | Ala | Ala | Ala | Leu | Ile | Leu | Ser | Lys | His | Pro | Thr |
| 225 |   |   |   |   | 230 |   |   |   |   | 235 |   |   |   |   | 240 |
| Trp | Thr | Asn | Ala | Gln | Val | Arg | Asp | Arg | Leu | Glu | Ser | Thr | Ala | Thr | Tyr |
|   |   |   |   | 245 |   |   |   |   | 250 |   |   |   |   | 255 |   |
| Leu | Gly | Asn | Ser | Phe | Tyr | Tyr | Gly | Lys | Gly | Leu | Ile | Asn | Val | Gln | Ala |
|   |   |   | 260 |   |   |   |   | 265 |   |   |   | 270 |   |   |   |
| Ala | Ala | Gln |   |   |   |   |   |   |   |   |   |   |   |   |   |
|   |   | 275 |   |   |   |   |   |   |   |   |   |   |   |   |   |

( 2 ) INFORMATION FOR SEQ ID NO:9:

( i ) SEQUENCE CHARACTERISTICS:
  ( A ) LENGTH: 274 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:9:

```
Ala Gln Thr Val Pro Tyr Gly Ile Pro Leu Ile Lys Ala Asp Lys Val
  1               5                  10                  15

Gln Ala Gln Gly Phe Lys Gly Ala Asn Val Lys Val Ala Val Leu Asp
             20                  25                  30

Thr Gly Ile Gln Ala Ser His Pro Asp Leu Asn Val Val Gly Gly Ala
         35                  40                  45

Ser Phe Val Ala Gly Glu Ala Tyr Asn Thr Asp Gly Asn Gly His Gly
     50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Ser Tyr Ser Gly Ile Val Ser Gly Ile Glu Trp
             100                 105                 110

Ala Thr Thr Asn Gly Met Asp Val Ile Asn Met Ser Leu Gly Gly Ala
         115                 120                 125

Ser Gly Ser Thr Ala Met Lys Gln Ala Val Asp Asn Ala Tyr Ala Arg
     130                 135                 140

Gly Val Val Val Val Ala Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                 165                 170                 175

Gly Ala Val Asp Ser Asn Ser Asn Arg Ala Ser Phe Ser Ser Val Gly
             180                 185                 190

Ala Glu Leu Glu Val Met Ala Pro Gly Ala Gly Val Tyr Ser Thr Tyr
         195                 200                 205

Pro Thr Asn Thr Tyr Ala Thr Leu Asn Gly Thr Ser Met Ala Ser Pro
     210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                 245                 250                 255

Gly Ser Ser Phe Tyr Tyr Gly Lys Gly Leu Ile Asn Val Glu Ala Ala
             260                 265                 270

Ala Gln
```

( 2 ) INFORMATION FOR SEQ ID NO:10:

( i ) SEQUENCE CHARACTERISTICS:
( A ) LENGTH: 269 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:10:

```
Ala Gln Ser Val Pro Trp Gly Ile Ser Arg Val Gln Ala Pro Ala Ala
  1               5                  10                  15

His Asn Arg Gly Leu Thr Gly Ser Gly Val Lys Val Ala Val Leu Asp
             20                  25                  30
```

```
Thr  Gly  Ile  Ser  Thr  His  Pro  Asp  Leu  Asn  Ile  Arg  Gly  Gly  Ala  Ser
          35                  40                       45

Phe  Val  Pro  Gly  Glu  Pro  Ser  Thr  Gln  Asp  Gly  Asn  Gly  His  Gly  Thr
     50                  55                       60

His  Val  Ala  Gly  Thr  Ile  Ala  Ala  Leu  Asn  Asn  Ser  Ile  Gly  Val  Leu
65                       70                       75                            80

Gly  Val  Ala  Pro  Ser  Ala  Glu  Leu  Tyr  Ala  Val  Lys  Val  Leu  Gly  Ala
               85                       90                            95

Ser  Gly  Ser  Gly  Ser  Val  Ser  Ile  Ala  Gln  Gly  Leu  Glu  Trp  Ala
               100                      105                 110

Gly  Asn  Asn  Gly  Met  His  Val  Ala  Asn  Leu  Ser  Leu  Gly  Ser  Pro  Ser
               115                 120                      125

Pro  Ser  Ala  Thr  Leu  Glu  Gln  Ala  Val  Asn  Ser  Ala  Thr  Ser  Arg  Gly
     130                      135                      140

Val  Leu  Val  Val  Ala  Ala  Ser  Gly  Asn  Ser  Gly  Ala  Gly  Ser  Ile  Ser
145                           150                      155                      160

Tyr  Pro  Ala  Arg  Tyr  Ala  Asn  Ala  Met  Ala  Val  Gly  Ala  Thr  Asp  Gln
                    165                      170                      175

Asn  Asn  Asn  Arg  Ala  Ser  Phe  Ser  Gln  Tyr  Gly  Ala  Gly  Leu  Asp  Ile
                    180                      185                      190

Val  Ala  Pro  Gly  Val  Asn  Val  Gln  Ser  Thr  Tyr  Pro  Gly  Ser  Thr  Tyr
          195                      200                      205

Ala  Ser  Leu  Asn  Gly  Thr  Ser  Met  Ala  Thr  Pro  His  Val  Ala  Gly  Ala
     210                      215                      220

Ala  Ala  Leu  Val  Lys  Gln  Lys  Asn  Pro  Ser  Trp  Ser  Asn  Val  Gln  Ile
225                      230                      235                           240

Arg  Asn  His  Leu  Lys  Asn  Thr  Ala  Thr  Ser  Leu  Gly  Ser  Thr  Asn  Leu
                    245                      250                      255

Tyr  Gly  Ser  Gly  Leu  Val  Asn  Ala  Glu  Ala  Ala  Thr  Arg
               260                      265
```

( 2 ) INFORMATION FOR SEQ ID NO:11:

( i ) SEQUENCE CHARACTERISTICS:
        ( A ) LENGTH: 1140 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
ATGAAGAAAC CGTTGGGGAA AATTGTCGCA AGCACCGCAC TACTCATTTC TGTTGCTTTT    60
AGTTCATCGA TCGCATCGGC TGCTGAAGAA GCAAAAGAAA AATATTTAAT TGGCTTTAAT   120
GAGCAGGAAG CTGTCAGTGA GTTTGTAGAA CAAGTAGAGG CAAATGACGA GGTCGCCATT   180
CTCTCTGAGG AAGAGGAAGT CGAAATTGAA TTGCTTCATG AATTTGAAAC GATTCCTGTT   240
TTATCCGTTG AGTTAAGCCC AGAAGATGTG GACGCGCTTG AACTCGATCC AGCGATTTCT   300
TATATTGAAG AGGATGCAGA AGTAACGACA ATGGCGCAAT CAGTGCCATG GGGAATTAGC   360
CGTGTGCAAG CCCCAGCTGC CCATAACCGT GGATTGACAG GTTCTGGTGT AAAAGTTGCT   420
GTCCTCGATA CAGGTATTTC CACTCATCCA GACTTAAATA TTCGTGGTGG CGCTAGCTTT   480
GTACCAGGGG AACCATCCAC TCAAGATGGG AATGGGCATG GCACGCATGT GGCCGGGACG   540
ATTGCTGCTT TAAACAATTC GATTGGCGTT CTTGGCGTAG CGCCGAGCGC GGAACTATAC   600
GCTGTTAAAG TATTAGGGGC GAGCGGTTCA GGTTCGGTCA GCTCGATTGC CCAAGGATTG   660
```

| | | | | | |
|---|---|---|---|---|---|
| GAATGGGCAG | GGAACAATGG | CATGCACGTT | GCTAATTTGA | GTTAGGAAG | CCCTTCGCCA | 720 |
| AGTGCCACAC | TTGAGCAAGC | TGTTAATAGC | GCGACTTCTA | GAGGCGTTCT | TGTTGTAGCG | 780 |
| GCATCTGGGA | ATTCAGGTGC | AGGCTCAATC | AGCTATCCGG | CCCGTTATGC | GAACGCAATG | 840 |
| GCAGTCGGAG | CTACTGACCA | AAACAACAAC | CGCGCCAGCT | TTCACAGTA | TGGCGCAGGG | 900 |
| CTTGACATTG | TCGCACCAGG | TGTAAACGTG | CAGAGCACAT | ACCCAGGTTC | AACGTATGCC | 960 |
| AGCTTAAACG | GTACATCGAT | GGCTACTCCT | CATGTTGCAG | GTGCAGCAGC | CCTTGTTAAA | 1020 |
| CAAAAGAACC | CATCTTGGTC | CAATGTACAA | ATCCGCAATC | ATCTAAAGAA | TACGGCAACG | 1080 |
| AGCTTAGGAA | GCACGAACTT | GTATGGAAGC | GGACTTGTCA | ATGCAGAAGC | GGCAACACGC | 1140 |

( 2 ) INFORMATION FOR SEQ ID NO:12:

( i ) SEQUENCE CHARACTERISTICS:
        ( A ) LENGTH: 1140 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| ATGAAGAAAC | CGTTGGGGAA | AATTGTCGCA | AGCACCGCAC | TACTCATTTC | TGTTGCTTTT | 60 |
| AGTTCATCGA | TCGCATCGGC | TGCTGAAGAA | GCAAAAGAAA | AATATTTAAT | TGGCTTTAAT | 120 |
| GAGCAGGAAG | CTGTCAGTGA | GTTTGTAGAA | CAAGTAGAGG | CAAATGACGA | GGTCGCCATT | 180 |
| CTCTCTGAGG | AAGAGGAAGT | CGAAATTGAA | TTGCTTCATG | AATTTGAAAC | GATTCCTGTT | 240 |
| TTATCCGTTG | AGTTAAGCCC | AGAAGATGTG | GACGCGCTTG | AACTCGATCC | AGCGATTTCT | 300 |
| TATATTGAAG | AGGATGCAGA | AGTAACGACA | ATGGCGCAAT | CAGTGCCATG | GGAATTAGC | 360 |
| CGTGTGCAAG | CCCCAGCTGC | CCATAACCGT | GGATTGACAG | GTTCTGGTGT | AAAAGTTGCT | 420 |
| GTCCTCGATA | CAGGTATTTC | CACTCATCCA | GACTTAAATA | TTCGTGGTGG | CGCTAGCTTT | 480 |
| GTACCAGGGG | AACCATCCAC | TCAAGATGGG | AATGGGCATG | GCACGCATGT | GGCCGGGACG | 540 |
| ATTGCTGCTT | TAGACAACTC | GATTGGCGTT | CTTGGCGTAG | CGCCGAGCGC | GGAACTATAC | 600 |
| GCTGTTAAAG | TATTAGGGGC | GAGCGGTTCA | GGCGCCATCA | GCTCGATTGC | CAAGGATTG | 660 |
| GAATGGGCAG | GGAACAATGG | CATGCACGTT | GCTAATTTGA | GTTAGGAAG | CCCTTCGCCA | 720 |
| AGTGCCACAC | TTGAGCAAGC | TGTTAATAGC | GCGACTTCTA | GAGGCGTTCT | TGTTGTAGCG | 780 |
| GCATCTGGGA | ATTCAGGTGC | AGGCTCAATC | AGCTATCCGG | CCCGTTATGC | GAACGCAATG | 840 |
| GCAGTCGGAG | CTACTGACCA | AAACAACAAC | CGCGCCAGCT | TTCACAGTA | TGGCGCAGGG | 900 |
| CTTGACATTG | TCGCACCAGG | TGTAAACGTG | CAGAGCACAT | ACCCAGGTTC | AACGTATGCC | 960 |
| AGCTTAAACG | GTACATCGAT | GGCTACTCCT | CATGTTGCAG | GTGCAGCAGC | CCTTGTTAAA | 1020 |
| CAAAAGAACC | CATCTTGGTC | CAATGTACAA | ATCCGCAATC | ATCTAAAGAA | TACGGCAACG | 1080 |
| AGCTTAGGAA | GCACGAACTT | GTATGGAAGC | GGACTTGTCA | ATGCAGAAGC | GGCAACACGC | 1140 |

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
TATGCCAGCC ACAACGGTAC TTCGATGGCT                                                    30
```

( 2 ) INFORMATION FOR SEQ ID NO:14:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
CACAGTTGCG GCTCTAGATA ACTCAATCGG T                                                  31
```

( 2 ) INFORMATION FOR SEQ ID NO:15:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
GCTGACGGTT CCGGCGCTAT TAGTTGGATC ATT                                                33
```